United States Patent
Hotter et al.

(10) Patent No.: US 10,189,860 B2
(45) Date of Patent: Jan. 29, 2019

(54) HYDRATES OF DOLUTEGRAVIR SODIUM

(71) Applicants: LEK PHARMACEUTICALS D.D., Ljubljana (SI); SANDOZ AG, Basel (CH)

(72) Inventors: Andreas Hotter, Kundl (AT); Andrea Thaler, Kundl (AT); Andrija Lebar, Ljubljana (SI); Biljana Jankovic, Ljubljana (SI); Klemen Naversnik, Ljubljana (SI); Uros Klancar, Ljubljana (SI); Zrinka Abramovic, Ljubljana (SI)

(*) Notice: Subject to any disclaimer, the term of this patent is extended or adjusted under 35 U.S.C. 154(b) by 0 days.

(21) Appl. No.: 15/329,673

(22) PCT Filed: Jul. 29, 2015

(86) PCT No.: PCT/EP2015/067329
§ 371 (c)(1),
(2) Date: Jan. 27, 2017

(87) PCT Pub. No.: WO2016/016279
PCT Pub. Date: Feb. 4, 2016

(65) Prior Publication Data
US 2017/0217987 A1   Aug. 3, 2017

(30) Foreign Application Priority Data

Jul. 29, 2014 (EP) .................... 14178989
Jul. 7, 2015 (EP) .................... 15175729

(51) Int. Cl.
   *C07D 498/14* (2006.01)
(52) U.S. Cl.
   CPC .................. *C07D 498/14* (2013.01)
(58) Field of Classification Search
   CPC .................................. C07D 498/14
   See application file for complete search history.

(56) References Cited

U.S. PATENT DOCUMENTS

2016/0347766 A1* 12/2016 Jetti ............... C07D 498/14

FOREIGN PATENT DOCUMENTS

| WO | 2010068253 | A1 |   | 6/2010 |           |
|----|------------|----|---|--------|-----------|
| WO | WO-2010068253 | A1 | * | 6/2010 | ........... A61K 31/351 |
| WO | 2011094150 | A1 |   | 8/2011 |           |
| WO | 2013038407 | A1 |   | 3/2013 |           |
| WO | 2014064409 | A1 |   | 5/2014 |           |
| WO | 2014184553 | A1 |   | 11/2014 |          |
| WO | 2015022351 |    |   | 2/2015 |           |

OTHER PUBLICATIONS

US Pharmacopeia (http://www.pharmacopeia.cn/v29240/usp29nf24s0_c941.html) 2005 Pharmacopeial Forum 31(4), pp. 1-6 (Year: 2005).*
Speakman, S.A. "Basics of X-Ray Powder Diffraction" (http://prism.mit.edu/xray/documents/1%20Basics%20of%20X-Ray%20Powder%20Diffraction.pdf) Available Nov. 28, 2014, pp. 1-97 (Year: 2014).*
PCT International Search Report and Written Opinion for PCT/EP2015/067329, dated Jan. 8, 2016, 15 pages.

* cited by examiner

*Primary Examiner* — Andrew S Rosenthal
(74) *Attorney, Agent, or Firm* — Luedeka Neely Group, P.C.

(57) ABSTRACT

The invention relates to novel hydrates of dolutegravir sodium and to processes for their preparation. Furthermore, the invention relates to a novel crystalline form of dolutegravir sodium, which is a useful intermediate for the preparation of one of the novel hydrates. In addition, the invention relates to the use of the novel hydrates for the production of pharmaceutical compositions. Finally, the invention relates to pharmaceutical compositions comprising an effective amount of the novel hydrates, to oral dosage forms comprising said pharmaceutical compositions, to a process for preparing said oral dosage forms, and to the use of said pharmaceutical compositions or dosage forms in the treatment of retroviral infections such as HIV-1 infections.

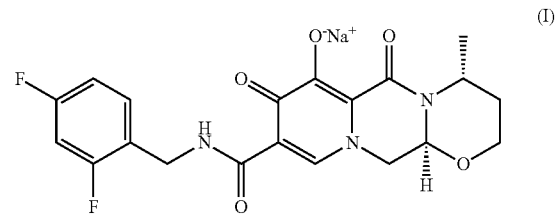

9 Claims, 14 Drawing Sheets a)

b)

a)

b)

HYDRATES OF DOLUTEGRAVIR SODIUM

This application is a Section 371 national phase entry of PCT application PCT/EP2015/067329, filed Jul. 29, 2015. This application also claims the benefit of the earlier filing dates of European patent application 14178989.1, filed Jul. 29, 2014, and of European patent application 15175729.1, filed Jul. 7, 2015.

FIELD OF THE INVENTION

The invention relates to novel hydrates of dolutegravir sodium and to processes for their preparation. Furthermore, the invention relates to a novel crystalline form of dolutegravir sodium, which is an useful intermediate for the preparation of one of the novel hydrates. In addition, the invention relates to the use of the novel hydrates for the production of pharmaceutical compositions. Finally, the invention relates to pharmaceutical compositions comprising an effective amount of the novel hydrates, to oral dosage forms comprising said pharmaceutical compositions, to a process for preparing said oral dosage forms, and to the use of said pharmaceutical compositions or dosage forms in the treatment of retroviral infections such as HIV-1 infections.

BACKGROUND OF THE INVENTION

Dolutegravir, chemically designated (4R,12aS)—N-(2,4-difluorobenzyl)-7-hydroxy-4-methyl-6,8-dioxo-3,4,6,8,12,12a-hexahydro-2H-pyrido[1',2':4,5]pyrazino[2,1-b][1,3]oxazine-9-carboxamide, is a human immunodeficiency virus type 1 (HIV-1) integrase strand transfer inhibitor (INSTI) indicated in combination with other antiretroviral agents for the treatment of HIV-1 infection. The marketed finished dosage form (TIVICAY™) contains dolutegravir as its sodium salt, chemically denominated sodium (4R,12aS)-9-((2,4-difluorobenzyl)carbamoyl)-4-methyl-6,8-dioxo-3,4,6,8,12,12a-hexahydro-2H-pyrido[1',2':4,5]pyrazino[2,1-b][1,3]oxazin-7-olate, which is represented by the following general chemical formula (I):

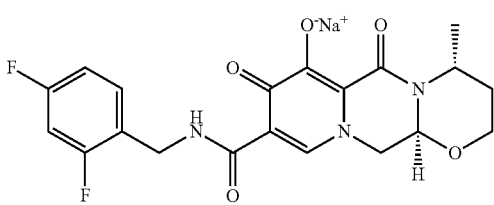

(I)

WO 2010/068253 A1 discloses a monohydrate and an anhydrous form of dolutegravir sodium as well as a crystalline form of the free compound. Processes for the preparation of said forms are also provided in the application.

WO 2013/038407 A1 discloses amorphous dolutegravir sodium and processes for preparing the same.

Hydrates of pharmaceutical drug substances are of particular interest as they provide new opportunities for preparing novel pharmaceutical compositions with improved quality, activity and/or compliance. This is due to the fact that hydrates have different physicochemical properties compared to their anhydrous counterparts such as melting point, density, habitus, chemical and physical stability, hygroscopicity, dissolution rate, solubility, bioavailability etc., which influence the formulation process and also impact the final drug product.

If an anhydrous form is selected, phase changes during the formulation process induced by hydrate formation must be avoided. This can be particularly difficult if for example wet granulation is used with a substance that is able to form hydrates like dolutegravir sodium. Hence, a stable hydrate of dolutegravir sodium would allow to easily formulate dolutegravir sodium in a controlled manner and subsequently also facilitate storage and packaging. However, the so far known dolutegravir sodium monohydrate disclosed in WO 2010/068253 A1 shows excessive water uptake when exposed to moisture and on the other hand already dehydrates below 30% relative humidity.

Therefore, there is a need for hydrates of dolutegravir sodium with improved physicochemical properties, e.g. for hydrates which are stable over a broad humidity range, in particular for hydrates absorbing only low amounts of water at elevated humidity and on the other hand preserving their crystal structure also at dry conditions. In addition, there is a need for pharmaceutical compositions comprising these hydrates, and thus also for hydrates that allow for improved formulation of dolutegravir sodium in pharmaceutical compositions.

SUMMARY OF THE INVENTION

The present invention relates to novel hydrates of dolutegravir sodium and to processes for their preparation. Specifically, the present invention provides crystalline forms of dolutegravir sodium of formula (I). The present invention also provides processes for their preparation. The present invention further provides uses for the crystalline forms and a pharmaceutical composition including the crystalline forms. The present invention also provides a process for the preparation of the pharmaceutical composition. The pharmaceutical composition for therapeutic use is also set forth.

The novel hydrates are physically and chemically stable over a broad humidity range, show only low water uptakes when exposed to moisture and are even stable at dry conditions. Therefore, the novel hydrates are especially suitable for the preparation of pharmaceutical compositions, e.g. in terms of time and costs.

In particular, it has been found that crystal Form HxA exhibits improved properties which allow for improved formulation of Form HxA in pharmaceutical compositions.

In addition, the present invention relates to a novel crystalline form of dolutegravir sodium, which, for the first time, allows the preparation of one of the novel hydrates and is therefore a valuable intermediate.

Aspects, advantageous features and preferred embodiments of the present invention are summarized in the following items:

1) A crystalline form HxA of a compound dolutegravir sodium characterized by a powder X-ray diffractogram comprising at least five characteristic peaks at 2-Theta angles selected from 7.9±0.2°, 9.4±0.2°, 11.4±0.2°, 11.6±0.2°, 12.5±0.2°, 12.8±0.2°, 13.6±0.2°, 15.2±0.2°, 15.9±0.2°, 18.4±0.2°, 19.1±0.2°, 19.8±0.2°, 20.0±0.2°, 20.8±0.2°, 22.9±0.2°, 23.3±0.2°, 24.4±0.2°, 25.2±0.2°, 26.0±0.2°, 27.1±0.2°, 28.4±0.2° and/or 29.4±0.2°, preferably measured with Cu—Kα radiation, more preferably measured with Cu—Kα$_{1,2}$ radiation having a wavelength of 0.15419 nm at room temperature.

2) A crystalline form HxA of a compound dolutegravir sodium characterized by a powder X-ray diffractogram comprising characteristic peaks at 2-Theta angles of 7.9±0.2°, 9.4±0.2°, 12.5±0.2°, 15.9±0.2° and 20.8±0.2°, preferably measured with Cu—Kα radiation, more preferably measured with Cu—Kα$_{1,2}$ radiation having a wavelength of 0.15419 nm at room temperature.

3) A crystalline form HxA of a compound dolutegravir sodium according to item 2) characterized by a powder X-ray diffractogram further comprising one or more additional characteristic peaks at 2-Theta angles of 11.4±0.2°, 11.6±0.2°, 13.6±0.2°, 15.2±0.2°, 18.4±0.2°, 19.1±0.2°, 19.8±0.2°, 22.9±0.2°, 23.3±0.2°, 24.4±0.2°, 26.0±0.2° and/or 27.1±0.2°, preferably measured with Cu—Kα radiation, more preferably measured with Cu—Kα$_{1,2}$ radiation having a wavelength of 0.15419 nm at room temperature.

4) A crystalline form HxA of a compound dolutegravir sodium according to item 2) characterized by a powder X-ray diffractogram further comprising one or more additional characteristic peaks at 2-Theta angles of 11.6±0.2°, 13.6±0.2°, 15.2±0.2°, 24.4±0.2° and/or 26.0±0.2°, preferably measured with Cu—Kα radiation, more preferably measured with Cu—Kα$_{1,2}$ radiation having a wavelength of 0.15419 nm at room temperature.

5) A crystalline form HxA of a compound dolutegravir sodium according to item 2) characterized by a powder X-ray diffractogram comprising characteristic peaks at 2-Theta angles of 7.9±0.2°, 9.4±0.2°, 11.6±0.2°, 12.5±0.2°, 13.6±0.2°, 15.2±0.2°, 15.9±0.2°, 20.8±0.2°, 24.4±0.2° and 26.0±0.2°, preferably measured with Cu—Kα radiation, more preferably measured with Cu—Kα$_{1,2}$ radiation having a wavelength of 0.15419 nm at room temperature.

6) A crystalline form HxA of a compound dolutegravir sodium according to item 2) or item 5) characterized by a powder X-ray diffractogram comprising characteristic peaks at 2-Theta angles of 7.9±0.2°, 9.4±0.2°, 11.4±0.2°, 11.6±0.2°, 12.5±0.2°, 13.6±0.2°, 15.2±0.2°, 15.9±0.2°, 18.4±0.2°, 19.1±0.2°, 19.8±0.2°, 20.8±0.2°, 22.9±0.2°, 23.3±0.2°, 24.4±0.2°, 26.0±0.2° and 27.1±0.2°, preferably measured with Cu—Kα radiation, more preferably measured with Cu—Kα$_{1,2}$ radiation having a wavelength of 0.15419 nm at room temperature.

7) A crystalline form HxA according to any of items 1 to 6 comprising 0.2 to 0.7 mol equivalents of water per mol dolutegravir sodium of formula (I) when measured at a relative humidity from 30 to 70% relative humidity and a temperature of 25±0.1° C.

8) A process for the preparation of the crystalline form HxA according to any one of items 1 to 7 comprising the steps of:
 (i) providing a suspension or a solution comprising dolutegravir in a solvent, preferably comprising at least 90 volume % methanol, more preferably about at least 95 volume % and most preferably about at least 99 volume %, wherein the suspension or the solution comprises more than 50 g, preferably at least 75 g, more preferably about 75 to 95 g, even more preferably about 75 to 85 g and most preferably about 75 to 80 g of dolutegravir per liter of solvent,
 (ii) reacting dolutegravir with sodium methoxide, preferably at a temperature of not more than 30° C., preferably at about not more than 20° C., more preferably at about not more than 10° C. and most preferably at about not more than 5° C., preferably for about 1 to 24 hours, more preferably for about 1 to 12 hours and most preferably for about 1 to 2 hours, preferably under stirring, and
 (iii) optionally, increasing the reaction temperature preferably to about 10 to 30° C., more preferably to about 15 to 30° C. and most preferably to about 20 to 25° C. and keeping the suspension or the solution at the applied temperature preferably for about 1 to 48 hours, more preferably for about 1 to 24 hours and most preferably for about 1 to 12 hours, preferably under stirring, and
 (iv) precipitating dolutegravir sodium.

Sodium methoxide may be applied as solid or methanolic solution. Solutions preferably have a sodium methoxide concentration of about 1 to 30 weight %, preferably of about 10 to 25 weight %, more preferably of about 20 to 25 weight % and most preferably of about 25 weight %. The ratio of dolutegravir and sodium methoxide employed is about 1.0:1.0 to 1.1, preferably a 1.0:1.0 ratio is used for the reaction.

9) A process according to item 8, further comprising
 (v) isolating dolutegravir sodium by separating at least a portion of the crystalline form HxA of dolutegravir sodium according to any one of the items 1 to 7 from its mother liquor, preferably by filtration or centrifugation, more preferably by filtration.

10) The process according to item 8, further comprising:
 (v) isolating obtained dolutegravir sodium by filtration or centrifugation, preferably by filtration.

11) A process according to item 9 or item 10, further comprising drying the crystalline form of dolutegravir sodium obtained in step (v) at a temperature of not more than 80° C., preferably of about not more than 50° C., more preferably at a temperature of about not more than 40° C., most preferably at a temperature of about 15° C. to 25° C.; and a vacuum of not more than 100 mbar, more preferably at about not more than 50 mbar and most preferably at about not more than 30 mbar.

12) The process according to any of items 8 to 11, wherein the step of precipitating dolutegravir sodium results in a mean volumetric particle size distribution (PSD) of d0.9 (μm) in a range of from 5 μm to less than 10 μm, determined by laser diffraction.

13) A crystalline form Hy1B of a compound dolutegravir sodium characterized by a powder X-ray diffractogram comprising at least five characteristic peaks at 2-Theta angles selected from 6.3±0.2°, 7.4±0.2°, 10.9±0.2°, 11.1±0.2°, 12.7±0.2°, 16.2±0.2, 18.6±0.2°, 18.8±0.2°, 19.7±0.2°, 20.5±0.2°, 21.0±0.2°, 22.1±0.2°, 23.0±0.2°, 24.0±0.2°, 24.9±0.2° and/or 26.5±0.2°, preferably measured with Cu—Kα radiation, more preferably measured with Cu—Kα$_{1,2}$ radiation having a wavelength of 0.15419 nm at room temperature.

14) A crystalline form Hy1B of a compound dolutegravir sodium characterized by a powder X-ray diffractogram comprising characteristic peaks at 2-Theta angles of 6.3±0.2°, 7.4±0.2°, 11.1±0.2°, 12.7±0.2° and 16.2±0.2°, preferably measured with Cu—Kα radiation, more preferably measured with Cu—Kα$_{1,2}$ radiation having a wavelength of 0.15419 nm at room temperature.

15) A crystalline form Hy1B of a compound dolutegravir sodium according to item 14) characterized by a powder X-ray diffractogram further comprising one or more additional characteristic peaks at 2-Theta angles of 10.9±0.2°, 18.6±0.2°, 18.8±0.2°, 19.7±0.2°, 20.5±0.2°, 21.0±0.2°, 22.1±0.2°, 23.0±0.2°, 24.0±0.2°, 24.9±0.2° and/or 26.5±0.2°, preferably measured with Cu—Kα radiation, more preferably measured with Cu—Kα$_{1,2}$ radiation having a wavelength of 0.15419 nm at room temperature.

16) A crystalline form Hy1B of a compound dolutegravir sodium according to item 14) characterized by a powder X-ray diffractogram further comprising one or more additional characteristic peaks at 2-Theta angles of 10.9±0.2°, 18.6±0.2°, 18.8±0.2°, 20.5±0.2°, 21.0±0.2° and/or 23.0±0.2°, preferably measured with Cu—Kα radiation, more preferably measured with Cu—K$\alpha_{1,2}$ radiation having a wavelength of 0.15419 nm at room temperature.

17) A crystalline form Hy1B of a compound dolutegravir sodium according to item 14) characterized by a powder X-ray diffractogram comprising characteristic peaks at 2-Theta angles of 6.3±0.2°, 7.4±0.2°, 10.9±0.2°, 11.1±0.2°, 12.7±0.2°, 16.2±0.2°, 18.6±0.2°, 18.8±0.2°, 20.5±0.2°, 21.0±0.2° and 23.0±0.2°, preferably measured with Cu—K$\alpha$ radiation, more preferably measured with Cu—K$\alpha_{1,2}$ radiation having a wavelength of 0.15419 nm at room temperature.

18) A crystalline form Hy1B of a compound dolutegravir sodium according to item 14) or item 16) characterized by a powder X-ray diffractogram comprising characteristic peaks at 2-Theta angles of 6.3±0.2°, 7.4±0.2°, 10.9±0.2°, 11.1±0.2°, 12.7±0.2°, 16.2±0.2°, 18.6±0.2°, 18.8±0.2°, 19.7±0.2°, 20.5±0.2°, 21.0±0.2°, 22.1±0.2°, 23.0±0.2°, 24.0±0.2°, 24.9±0.2° and 26.5±0.2°, preferably measured with Cu—K$\alpha$ radiation, more preferably measured with Cu—K$\alpha_{1,2}$ radiation having a wavelength of 0.15419 nm at room temperature.

19) A crystalline form Hy1B according to any of items 13 to 18 comprising 0.7 to 1.3 mol equivalents of water per mol dolutegravir sodium when measured at a relative humidity from 30 to 90% and a temperature of 25±0.1° C.

20) A process for the preparation of the crystalline form Hy1B according to any one of the items 13 to 19 comprising subjecting the crystalline form S$_{EtOH/H2O}$ according to any one of items 21 to 27 to an atmosphere having a relative humidity of at least 75±5% and a temperature of at least 40° C., preferably for about 12 to 168 hours, more preferably for about 12 to 72 hours and most preferably for about 12 to 24 hours.

21) A crystalline form S$_{EtOH/H2O}$ of a compound dolutegravir sodium characterized by a powder X-ray diffractogram comprising at least five characteristic peaks at 2-Theta angles selected from 6.5±0.2°, 7.0±0.2°, 10.6±0.2°, 11.0±0.2°, 13.3±0.2°, 16.0±0.2°, 18.0±0.2°, 19.1±0.2°, 20.3±0.2°, 20.8±0.2° and/or 22.6±0.2°, preferably measured with Cu—K$\alpha$ radiation, more preferably measured with Cu—K$\alpha_{1,2}$ radiation having a wavelength of 0.15419 nm at room temperature.

22) A crystalline form S$_{EtOH/H2O}$ of a compound dolutegravir sodium characterized by a powder X-ray diffractogram comprising characteristic peaks at 2-Theta angles of 6.5±0.2°, 7.0±0.2°, 13.3±0.2°, 16.0±0.2° and 22.6±0.2°, preferably measured with Cu—K$\alpha$ radiation, more preferably measured with Cu—K$\alpha_{1,2}$ radiation having a wavelength of 0.15419 nm at room temperature.

23) A crystalline form S$_{EtOH/H2O}$ of a compound dolutegravir sodium according to item 22) characterized by a powder X-ray diffractogram further comprising one or more additional characteristic peaks at 2-Theta angles of 10.6±0.2°, 11.0±0.2°, 18.0±0.2°, 19.1±0.2°, 20.3±0.2° and/or 20.8±0.2°, preferably measured with Cu—K$\alpha$ radiation, more preferably measured with Cu—K$\alpha_{1,2}$ radiation having a wavelength of 0.15419 nm at room temperature.

24) A crystalline form S$_{EtOH/H2O}$ of a compound dolutegravir sodium according to item 22) characterized by a powder X-ray diffractogram further comprising one or more additional characteristic peaks at 2-Theta angles of 10.6±0.2°, 11.0±0.2°, 18.0±0.2°, 19.1±0.2° and/or 20.3±0.2°, preferably measured with Cu—K$\alpha$ radiation, more preferably measured with Cu—K$\alpha_{1,2}$ radiation having a wavelength of 0.15419 nm at room temperature.

25) A crystalline form S$_{EtOH/H2O}$ of a compound dolutegravir sodium according to item 22) characterized by a powder X-ray diffractogram comprising characteristic peaks at 2-Theta angles of 6.5±0.2°, 7.0±0.2°, 10.6±0.2°, 11.0±0.2°, 13.3±0.2°, 16.0±0.2°, 18.0±0.2°, 19.1±0.2°, 20.3±0.2° and 22.6±0.2°, preferably measured with Cu—K$\alpha$ radiation, more preferably measured with Cu—K$\alpha_{1,2}$ radiation having a wavelength of 0.15419 nm at room temperature.

26) A crystalline form S$_{EtOH/H2O}$ of a compound dolutegravir sodium according to item 22) or item 25 characterized by a powder X-ray diffractogram comprising characteristic peaks at 2-Theta angles of 6.5±0.2°, 7.0±0.2°, 10.6±0.2°, 11.0±0.2°, 13.3±0.2°, 16.0±0.2°, 18.0±0.2°, 19.1±0.2°, 20.3±0.2°, 20.8±0.2° and 22.6±0.2°, preferably measured with Cu—K$\alpha$ radiation, more preferably measured with Cu—K$\alpha_{1,2}$ radiation having a wavelength of 0.15419 nm at room temperature.

27) The crystalline form S$_{EtOH/H2O}$ according to any of items 21 to 26 comprising 0.3 mol equivalents of ethanol and 0.2 mol equivalents of water per mol dolutegravir sodium when measured at a relative humidity of 25% and a temperature from 15 to 25° C.

28) A process for the preparation of the crystalline form S$_{EtOH/H2O}$ according to any one of items 21 to 27 comprising the steps of:
 (i) providing a suspension or a solution of dolutegravir in a solvent comprising at least 90 volume % ethanol, preferably about at least 96 volume % ethanol and more preferably about at least 99 volume % ethanol, preferably comprising about 10 to 100 g, more preferably about 10 to 50 g and most preferably about 10 to 25 g of dolutegravir per liter solvent
 (ii) reacting dolutegravir with sodium ethoxide at a temperature of not more than 45° C., preferably at a temperature of not more than 40° C., preferably at about not more than 35° C., and most preferably at about not more than 30° C., preferably for about 1 to 24 hours, more preferably for about 1 to 12 hours, even more preferably for about 1 to 6 hours and most preferably for about 1 to 2 hours, preferably under stirring, and
 (iii) precipitating dolutegravir sodium.

Sodium methoxide may be applied as solid or methanolic solution Solutions preferably have a sodium methoxide concentration of about 1 to 25 weight %, preferably of about 10 to 21 weight %, and most preferably of about 21 weight %. The ratio of dolutegravir and sodium ethoxide employed is about 1.0:0.8 to 2.0, preferably about 1.0:0.9 to 1.5, more preferably about 1.0:0.9 to 1.2 and most preferably a 1.0:1.0 ratio is used.

29) The process according to item 28, further comprising
 (iv) isolating dolutegravir sodium by separating at least a portion of the crystalline form S$_{EtOH/H2O}$ of dolutegravir sodium according to any one of the items 21 to 27 from its mother liquor, preferably by filtration or centrifugation, more preferably by filtration.

30) The process according to item 28, further comprising:
 (iv) isolating obtained dolutegravir sodium by filtration or centrifugation, preferably by filtration.

31) The process according to item 29 or item 30, further comprising drying the crystalline form S$_{EtOH/H2O}$ of dolutegravir sodium obtained in step (iv) at a temperature of not more than 80° C., preferably of about not more than 50° C., more preferably at a temperature of about not more than 40° C., most preferably at a temperature of about 15° C. to 25° C.; and a vacuum of not more than 100 mbar, more preferably at about not more than 50 mbar and most preferably at about not more than 30 mbar.

32) Use of the crystalline form HxA according to any one of items 1 to 7 or the crystalline form Hy1B according to any one of items 13 to 19 or mixtures thereof for the preparation of a pharmaceutical composition.

33) Use of the crystalline forms obtainable or obtained by a process according to any one of items 8 to 11 or item 20 or mixtures thereof for the preparation of a pharmaceutical composition.

34) A pharmaceutical composition comprising an effective amount of the crystalline form HxA according to any one of items 1 to 7 or the crystalline form Hy1B according to any one of items 13 to 19 or mixtures thereof and at least one pharmaceutically acceptable excipient.

35) A pharmaceutical composition comprising an effective amount of the crystalline forms obtainable or obtained by a process according to any one of items 8 to 11 or item 20 or mixtures thereof and at least one pharmaceutically acceptable excipient.

36) The pharmaceutical composition according to item 34 or item 35 for use in a method for the treatment treating of human immunodeficiency virus type 1 (HIV-1) infection in human.

37) Use of the crystalline form according to any one of items 20 to 26 for the preparation of the crystalline form Hy1B according to any one of items 12 to 18.

38) Use of the crystalline form obtainable or obtained by a process according to any one of items 28 to 31 for the preparation of the crystalline form Hy1B according to any one of items 13 to 19.

39) The pharmaceutical composition according to item 34, comprising a therapeutically effective amount of the crystalline form of items 1 to 7 and one or more pharmaceutically acceptable excipients selected from the group consisting of diluent/filler, binder, disintegrant, lubricant, and surfactant.

40) The pharmaceutical composition according to item 39, wherein
the diluent/filler is selected from the group consisting of sugar, cellulose or a derivative thereof, starch, calcium phosphate, calcium or magnesium carbonate, and mixtures thereof, preferably, the diluent/filler is microcrystalline cellulose and/or D-mannitol;
the binder is selected from the group consisting of povidone, tragacanth, sodium alginate, gum arabic, starch pregelatinized, gelatin and cellulosic derivates, preferably the binder is povidone;
the disintegrant is selected from the group consisting of croscarmellose sodium, sodium carboxymethyl starch, cross-linked polyvinylpyrrolidone, sodium carboxymethyl glycolate, sodium starch glycolate, low-substituted hydroxypropyl cellulose, citric acid and sodium bicarbonate, preferably the disintegrant is sodium starch glycolate;
the lubricant is selected from the group consisting of colloidal silicon dioxide (such as Aerosil®), talc, stearic acid, magnesium stearate, calcium stearate, zinc stearate, glyceryl behenate, sodium stearyl fumarate, polyethylene glycol, and silicon dioxide, preferably the lubricant is sodium stearyl fumarate;
the surfactant is selected from the group consisting of tween such as tween 80, polyoxyethylene-polyoxypropylene copolymer and sodium lauryl sulfate, preferably the surfactant is sodium lauryl sulfate.

41) The pharmaceutical composition according to item 39 or 40, wherein
the crystalline form of items 1 to 7 is present in an amount of from 5% to 30%, preferably of from 10% to 25%, more preferably of from 12% to 20%, and most preferably of from 15% to 19% by weight of the total weight of the pharmaceutical composition without coating, if present;
the diluent/filler is present in the pharmaceutical composition in an amount of from 0 to 90% by weight, preferably of from 20% to 80% by weight, more preferably of from 40% to 70% by weight, and most preferably of from 50% to 70% by weight of the total weight of the pharmaceutical composition without coating, if present;
the binder is present in the pharmaceutical composition in an amount of from 0 to 40% by weight, preferably of from 1% to 20% by weight, more preferably of from 2% to 10% by weight, and most preferably of from 3% to 8% by weight of the total weight of the pharmaceutical composition without coating, if present;
the disintegrant is present in the pharmaceutical composition in an amount of from 0 to 40% by weight, preferably of from 1% to 20% by weight, more preferably of from 2% to 10% by weight, and most preferably of from 3% to 8% by weight of the total weight of the pharmaceutical composition without coating, if present;
the lubricant is present in the pharmaceutical composition in an amount of from 0 to 10% by weight, preferably of from 0.1% to 8% by weight, more preferably of from 1% to 5% by weight, and most preferably of from 1% to 3% by weight of the total weight of the pharmaceutical composition without coating, if present;
the surfactant is present in the pharmaceutical composition in an amount of from 0 to 5% by weight, preferably of from 0.5% to 4% by weight, more preferably of from 1% to 3% by weight, and most preferably of from 1% to 2% by weight of the total weight of the pharmaceutical composition without coating, if present.

42) The pharmaceutical composition according to any of items 39 to 41, wherein the pharmaceutically acceptable excipients that are present in said composition are at least one diluent/filler, a binder, a disintegrant, and a lubricant, wherein the respective excipients are different from each other.

43) The pharmaceutical composition according to item 42, wherein said composition comprises mannitol, preferably D-mannitol, microcrystalline cellulose, povidone, sodium starch glycolate, and sodium stearyl fumarate, as the pharmaceutically acceptable excipients.

44) A process for preparing a pharmaceutical composition, comprising the steps of:
(I) providing the crystalline form of dolutegravir sodium of formula (I) of items 1 to 7;
(II) mixing the crystalline form of step (I) with the pharmaceutical excipients as defined in any of items 40 to 43;
(III) obtaining the pharmaceutical composition.

45) The process according to item 44, wherein step (II) comprises:
(II-1) mixing together crystalline form of dolutegravir sodium of formula (i) of items 1 to 7 and at least one diluent/filler;
(II-2) sieving the obtained mixture of step (II-1) through an appropriate mesh size, preferably through a mesh sieve of from 0.5 mm to 2.0 mm, more preferably of 0.7 mm;
(II-3) adding binder and disintegrant;
(II-4) mixing the mixture of step (II-3);
(II-5) adding sieved lubricant; and
(II-6) blending the mixture of step (II-5).

46) The pharmaceutical composition according to any of items 39 to 43, being in the form of an oral dosage form, preferably a solid oral dosage form.

47) The oral dosage form according to item 46, wherein the oral dosage form is a solid oral dosage form, preferably a capsule, tablet, pellet, or sachet, more preferably the solid oral dosage form is a tablet.

48) The oral dosage form according to item 46 or 47, wherein at least 75% of the dolutegravir sodium of formula (I) of items 1 to 7 of the total amount of the dolutegravir present in the dosage form are dissolved in 45 minutes or less when measured using USP paddle Apparatus 2 at 50 rpm in 0.9% NaCl, pH 6.8 phosphate buffer, and water.

49) A process for preparing oral dosage forms, comprising the steps of:
(i) providing the crystalline form of dolutegravir sodium of formula (I) of items 1 to 7, and the pharmaceutical excipients as defined in any of items 40 to 43;
(ii) formulating the crystalline form of dolutegravir sodium of formula (I) and pharmaceutical excipients of step (i) into an oral dosage form, wherein in step (ii) no wet granulation step, preferably no granulation step at all, is applied, more preferably step (ii) comprises a direct compression process;
(iii) obtaining said oral dosage form.

Step (i) of item 49 can be carried out according to the process according to items 44 and 45.

50) The process according to item 49, wherein the oral dosage form is a solid oral dosage form, preferably a capsule, tablet, pellet, or sachet, and most preferably the solid oral dosage form is a tablet.

51) The process according to item 50, wherein in a further step (iv) a coating is applied onto the oral dosage form obtained in step (iii).

52) The process according to item 51, wherein the oral dosage form is a film coated tablet.

53) The process according to item 44 or 45, or any of items 49 to 52, wherein the process does not include a step that is directed to reducing the size of the crystalline form of dolutegravir sodium of formula (I) of items 1 to 7, e.g. a micronization step.

54) The process according to item 44 or 45, or any of items 49 to 53, wherein the crystalline form of dolutegravir sodium of formula (I) of items 1 to 7 is prepared by the process of any of items 8 to 11.

55) The process according to item 44 or 45, or any of items 49 to 54, wherein the crystalline form of dolutegravir sodium of formula (I) of items 1 to 7, and the pharmaceutical excipients as provided in step (i) correspond to a pharmaceutical composition of any of items 39 to 43, or an oral dosage form of item 46, or a solid oral dosage form of items 47 or 48.

56) The pharmaceutical composition according to any of items 39 to 43, or the dosage form according to any of items 46 to 48, for use in a method for treating immunodeficiency virus type 1 (HIV-1) infection in human.

In the context of the present invention the following abbreviations have the indicated meaning, unless explicitly stated otherwise:
PXRD powder X-ray diffraction/diffractogram
TGA thermogravimetric analyses
DSC differential scanning calorimetry
GMSD gravimetric moisture sorption/desorption
$^1$H-NMR proton nuclear magnetic resonance
RT room temperature
RH relative humidity
m mass
V volume
MH monohydrate
MeOH methanol
conc. concentration
PSD Particle size distribution
DLG Dolutegravir
LC liquid cromatography

DETAILED DESCRIPTION OF THE INVENTION

Figure 1:
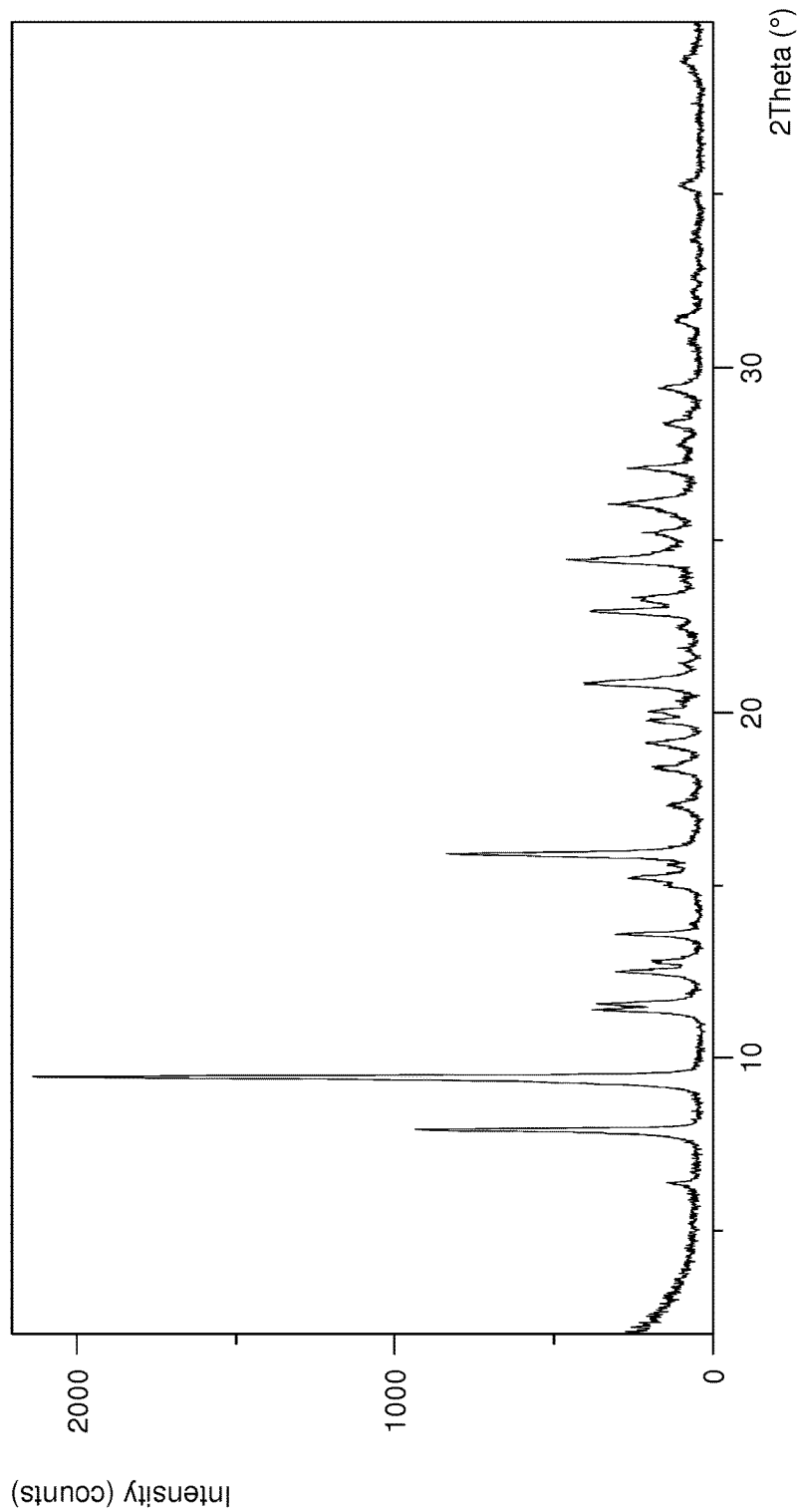
FIG. 1: Representative PXRD of dolutegravir sodium form HxA

The invention is described below in further detail by embodiments, without being limited thereto.

As used herein the term "room temperature" indicates that the applied temperature is not critical and that no exact temperature value has to be kept. Usually, "room temperature" is understood to mean temperatures between 15 and 25° C. [see e.g. European Pharmacopoeia 8.2, 1.2 (2014)].

The term "peaks" used herein corresponds to its typical meaning in the art of XRPD. It may generally mean peaks clearly visible in XRPD patterns. Further, a "peak" may, in a corresponding XRPD pattern, resemble a single peak at a given specified position, or it may represent a double-peak or multiple peaks around a given specified (central) position of the denoted "peak".

The term "essentially the same" with reference to PXRD means that variabilities in peak positions and relative intensities of the peaks are to be taken into account. For example, a typical precision of the 2-Theta values is in the range of ±0.2° 2-Theta. Thus, the diffraction peak of form HxA that usually appears at 9.4° 2-Theta for example can appear between 9.2° and 9.6° 2-Theta on most X-ray diffractometers under standard conditions. Furthermore, one skilled in the art will appreciate that relative peak intensities will show inter-apparatus variability as well as variability due to degree of crystallinity, preferred orientation, sample preparation and other factors known to those skilled in the art and should be taken as qualitative measure only.

The term "primary particle" means particles that are not, or not yet, assembled together. Characteristically, primary particles assemble in order to form e.g. agglomerates or aggregates. Thus, agglomerates can be an assembly of primary particles, and aggregates can develop when primary particles begin to form a common crystal-line structure. In other words, aggregates are an assembly of primary particles that have grown together and are aligned side by side.

In an aspect, the present invention relates to a novel hydrate of dolutegravir sodium, above and hereinafter also designated form HxA.

Form HxA is a monosodium salt of dolutegravir. Its molar ratio of dolutegravir and sodium typically and preferably lies in a range of about 1.0:0.9 to 1.1, more preferably of about 1.0:1.0.

Form HxA can be characterized by a PXRD comprising at least five peaks at 2-Theta angles selected from 7.9±0.2°, 9.4±0.2°, 11.4±0.2°, 11.6±0.2°, 12.5±0.2°, 12.8±0.2°, 13.6±0.2°, 15.2±0.2°, 15.9±0.2°, 18.4±0.2°, 19.1±0.2°, 19.8±0.2°, 20.0±0.2°, 20.8±0.2°, 22.9±0.2°, 23.3±0.2°, 24.4±0.2°, 25.2±0.2°, 26.0±0.2°, 27.1±0.2°, 28.4±0.2° and/or 29.4±0.2°.

Preferably, form HxA is characterized by a PXRD comprising characteristic peaks at 2-Theta angles of 7.9±0.2°, 9.4±0.2°, 12.5±0.2°, 15.9±0.2° and 20.8±0.2°. Form HxA may be further characterized by a PXRD further comprising one or more additional characteristic peaks at 2-Theta angles of 11.4±0.2°, 11.6±0.2°, 13.6±0.2°, 15.2±0.2°, 18.4±0.2°, 19.1±0.2°, 19.8±0.2°, 22.9±0.2°, 23.3±0.2°, 24.4±0.2°, 26.0±0.2° and/or 27.1±0.2°. Preferably, form HxA may be further characterized by a PXRD further comprising one or more additional characteristic peaks at 2-Theta angles of 11.6±0.2°, 13.6±0.2°, 15.2±0.2°, 24.4±0.2° and/or 26.0±0.2°.

More preferably, form HxA is characterized by a PXRD comprising characteristic at 2-Theta angles of 7.9±0.2°, 9.4±0.2°, 11.6±0.2°, 12.5±0.2°, 13.6±0.2°, 15.2±0.2°, 15.9±0.2°, 20.8±0.2°, 24.4±0.2° and 26.0±0.2°.

Even more preferably, form HxA is characterized by a PXRD comprising characteristic at 2-Theta angles of 7.9±0.2°, 9.4±0.2°, 11.4±0.2°, 11.6±0.2°, 12.5±0.2°, 13.6±0.2°, 15.2±0.2°, 15.9±0.2°, 18.4±0.2°, 19.1±0.2°, 19.8±0.2°, 20.8±0.2°, 22.9±0.2°, 23.3±0.2°, 24.4±0.2°, 26.0±0.2° and 27.1±0.2°.

Even more preferably, form HxA is characterized by a PXRD comprising characteristic at 2-Theta angles of 7.9±0.2°, 9.4±0.2°, 11.4±0.2°, 11.6±0.2°, 12.5±0.2°, 12.8±0.2°, 13.6±0.2°, 15.2±0.2°, 15.9±0.2°, 18.4±0.2°, 19.1±0.2°, 19.8±0.2°, 20.0±0.2°, 20.8±0.2°, 22.9±0.2°, 23.3±0.2°, 24.4±0.2°, 25.2±0.2°, 26.0±0.2°, 27.1±0.2°, 28.4±0.2° and 29.4±0.2°.

XPRDs of form HxA according to the above aspect are measured preferably with Cu—Kα radiation, more preferably with Cu—Kα$_{1,2}$ radiation having a wavelength of 0.15419 nm at room temperature.

A representative PXRD of form HxA is displayed in FIG. 1 herein. Additionally, form HxA can be characterized by showing a PXRD essentially the same as displayed in FIG. 1 when measured at room temperature with Cu—Kα$_{1,2}$ radiation having a wavelength of 0.15419 nm.

Figure 2:
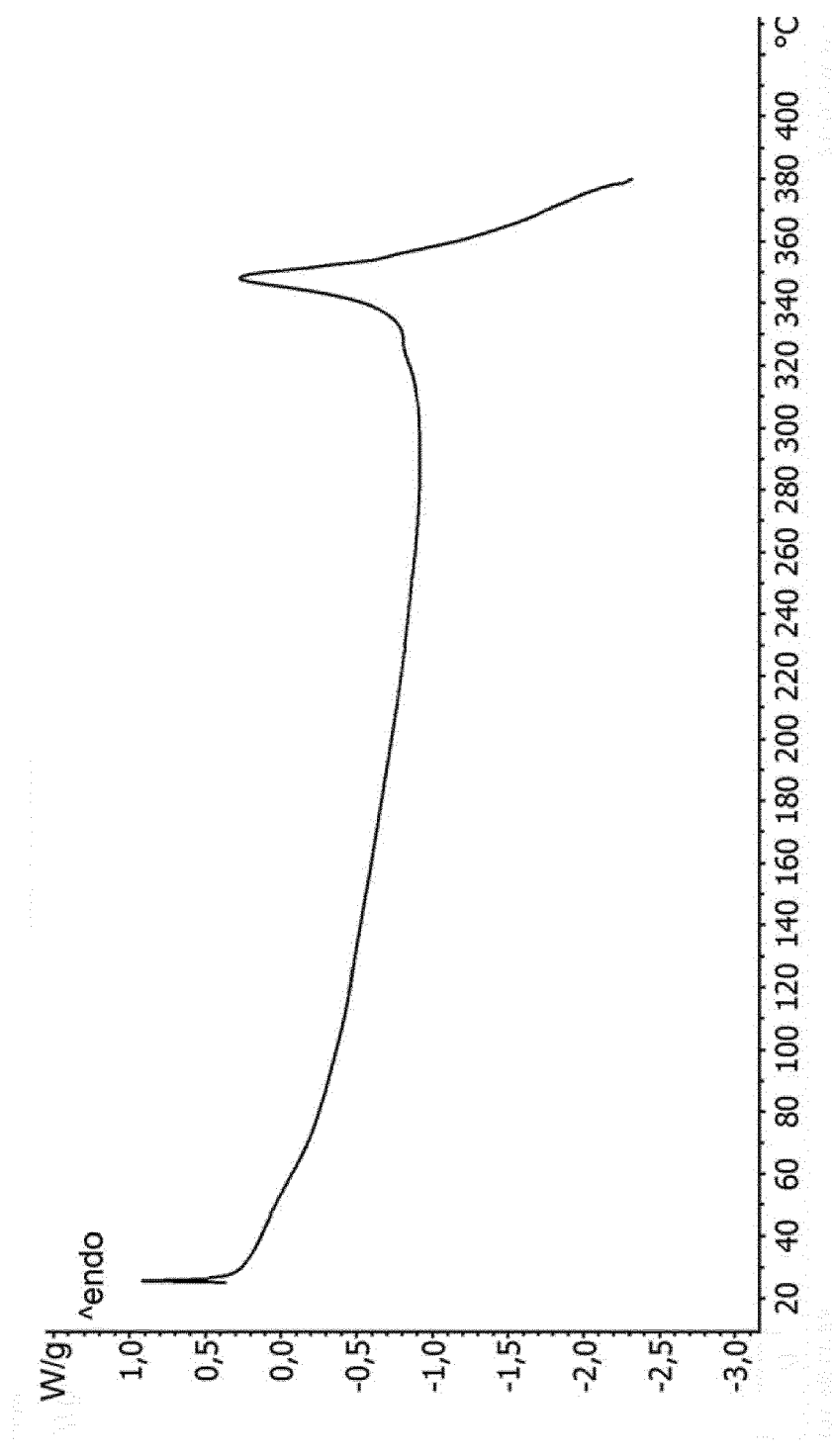
FIG. 2: Representative DSC curve of dolutegravir sodium form HxA equilibrated at about 30% RH and RT

Furthermore, a representative DSC curve of form HxA equilibrated at about 30% RH and RT is displayed in FIG. 2 herein. The DSC curve of form HxA shows an endotherm at about 330 to 355° C. with an onset temperature of about 338° C. and a peak maximum at about 348° C. which is due to melting and decomposition respectively.

Therefore, alternatively or additionally, form HxA can be characterized by a DSC curve comprising an endotherm at 330 to 355° C. when measured at a heating rate of 10° C./min.

Figure 3:
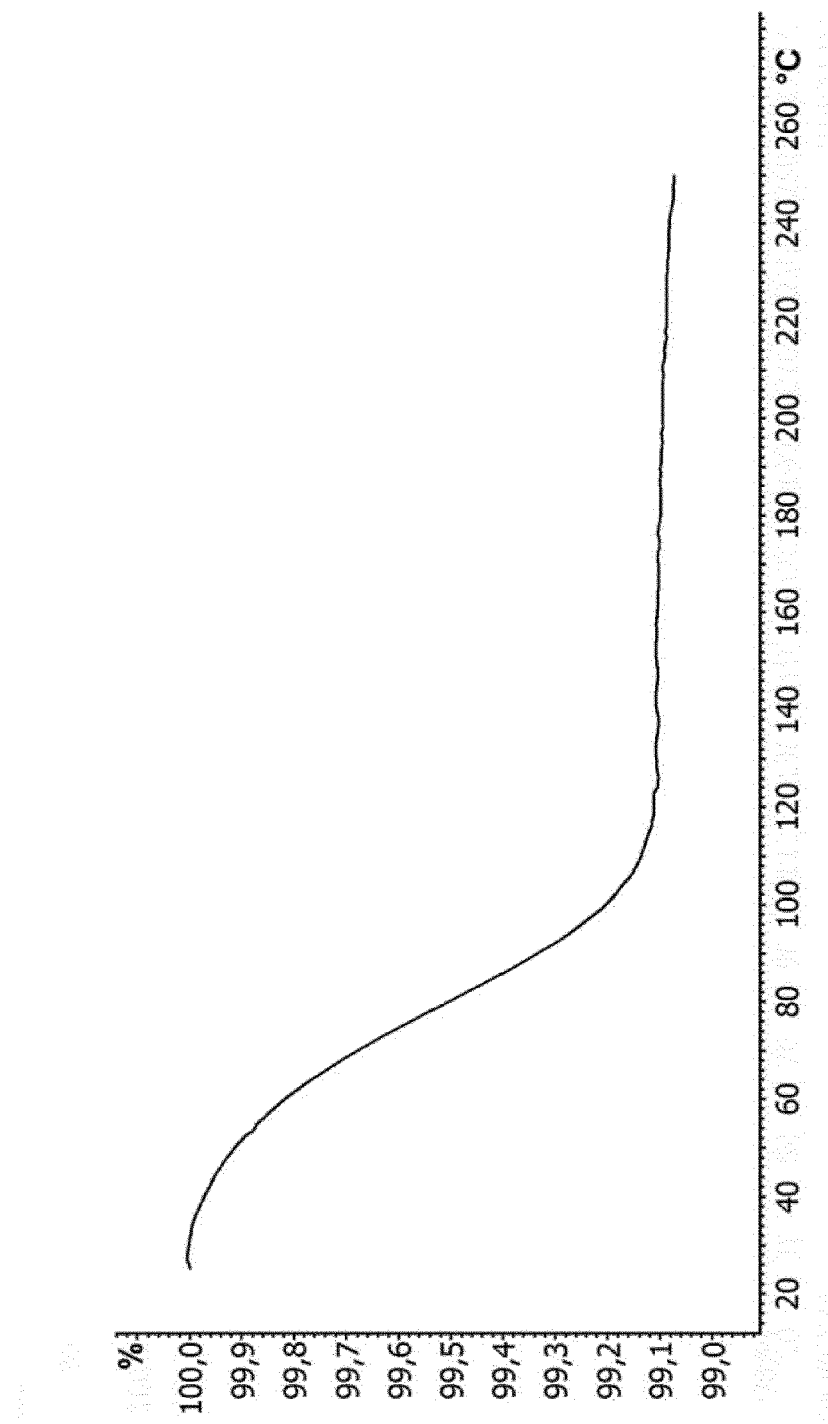
FIG. 3: Representative TGA curve of dolutegravir sodium form HxA equilibrated at about 30% RH and RT

In addition, a representative TGA curve of form HxA equilibrated at about 30% RH and RT is provided in FIG. 3 herein. The TGA curve of form HxA shows a weight loss of about 0.9% from 25 to 120° C. Coulometric Karl-Fischer titration of form HxA equilibrated at about 30% RH and RT revealed a water content of about 0.9% corresponding to 0.2 mol of water per mol of dolutegravir sodium. No organic solvent, in particular no methanol was traceable by $^1$H-NMR.

Hence, alternatively or additionally, form HxA can be characterized by comprising not more than 0.5%, preferably not more than 0.4%, more preferably not more than 0.3% and most preferably not more than 0.2%, for example not more than 0.1% organic solvent. Alternatively or additionally, form HxA can be characterized by comprising not more than 0.3%, preferably not more than 0.2%, more preferably not more than 0.1% and most preferably not more than 0.05% methanol.

Figure 10:
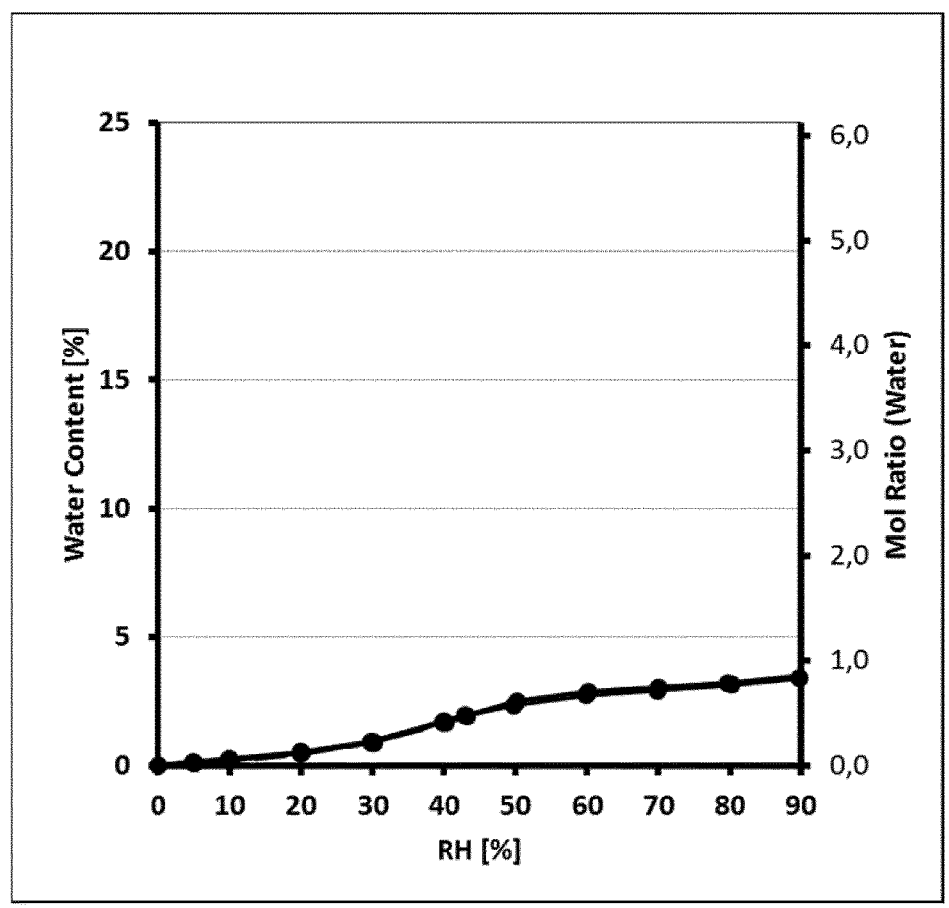
FIG. 10: Gravimetric moisture sorption/desorption isotherms of dolutegravir sodium form HxA

Representative gravimetric moisture sorption/desorption isotherms of form HxA are displayed in FIG. 10 herein. Form HxA, for example, shows a water content of about 0.9% corresponding to 0.2 mol of water per mol of dolutegravir sodium at about 30% RH and a water content of about 2.9 to 3.0% corresponding to 0.7 mol of water per mol of dolutegravir sodium at about 70% RH measured at temperature of 25±0.1° C. At 95% RH and 25±0.1° C. the sample shows a maximum water content of about 3.8%, which corresponds to 0.9 mol of water per mol of dolutegravir sodium. From the GMSD isotherms displayed in FIG. 10 herein it becomes clear that water uptake and loss respectively are reversible and that the water content of form HxA depends on the relative humidity of the surrounding atmosphere, which is typical for non-stoichiometric hydrates.

Therefore, alternatively or additionally, form HxA can be characterized by comprising 0.2 to 0.7 mol of water per mol of dolutegravir sodium when measured at temperature of 30 to 70% RH and 25±0.1° C.

Furthermore, in a further aspect the present invention relates to a process for the preparation of form HxA of dolutegravir sodium comprising the steps of:
(i) providing a suspension or a solution of dolutegravir in a solvent comprising methanol, wherein the suspension or the solution comprises more than 50 g, preferably at least 75 g dolutegravir per liter solvent,
(ii) reacting dolutegravir with sodium methoxide at a temperature of about not more than 30° C. and
(iii) precipitating dolutegravir sodium.

Dolutegravir, which is used as starting material for form HxA production can for example be prepared in accordance with the procedures disclosed in examples 1a to 1k or 3a to 3k of WO 2010/068253 A1.

In a first step, a suspension or a solution, preferably a suspension, of dolutegravir in a solvent comprising methanol is prepared. Preferably, the methanol concentration of the solvent used for preparing the mixture is about at least 90 volume %, more preferably about at least 95 volume % and most preferably about at least 99 volume %. Moreover, the water content of the solvent preferably is about not more than 10 volume %, more preferably about not more than 5 volume % and most preferably about not more than 1 volume %.

Essentially, the initial suspension or solution comprises more than 50 g, preferably about at least 75 g dolutegravir per liter solvent, for example about 75 to 100 g, more preferably about 75 to 95 g, even more preferably about 75 to 85 g and most preferably about 75 to 80 g dolutegravir per liter solvent may be applied.

In a next step dolutegravir is reacted with sodium methoxide by adding sodium methoxide to the suspension or the solution or vice versa. Sodium methoxide may be applied as solid or methanolic solution, whereas solutions which may be applied in the present process preferably have a sodium methoxide concentration of about 1 to 30 weight %, preferably of about 10 to 25 weight %, more preferably of about 20 to 25 weight % and most preferably of about 25 weight %. The ratio of dolutegravir and sodium methoxide employed is about 1.0:1.0 to 1.1, preferably a 1.0:1.0 ratio is used for the reaction.

Essentially, when combining sodium methoxide and dolutegravir, the reaction temperature is kept at about not more than 30° C., preferably at about not more than 20° C., more preferably at about not more than 10° C. and most preferably at about not more than 5° C. The suspension or the solution is preferably kept at the applied temperature for about 1 to 24 hours, more preferably for about 1 to 12 hours and most preferably for about 1 to 2 hours, preferably under stirring. Thereafter, the reaction temperature is increased preferably to about 10 to 30° C., more preferably to about 15 to 30° C. and most preferably to about 20 to 25° C. The suspension or the solution is preferably kept at the applied temperature for about 1 to 48 hours, more preferably for about 1 to 24 hours and most preferably for about 1 to 12 hours, preferably under stirring.

Subsequently, at least a portion of the obtained dolutegravir sodium crystals may be collected by any conventional method such as filtration or centrifugation, preferably by filtration.

Finally, the isolated dolutegravir sodium crystals may be dried at a temperature of about not more than 80° C., preferably of about not more than 60° C., more preferably of about not more than 50° C. and most preferably the crystals are dried at a temperature of about not more than 40° C. for example at about room temperature. Drying may be performed for about 1 to 72 hours, preferably for about 2 to 48 hours, more preferably for about 4 to 24 hours and most preferably for about 6 to 18 hours. Drying may be performed under vacuum preferably at about not more than 100 mbar, more preferably at about not more than 50 mbar and most preferably at about not more than 30 mbar, for example at about 20 to 30 mbar.

Preferably, the crystals that are obtained after precipitating dolutegravir sodium (form HxA) have a mean volumetric particle size distribution (PSD) with d0.9 (μm) in a range of from 5 μm to less than 10 μm. The mean volumetric particle size distribution (PSD) can be determined by common laser diffraction. In particular, dolutegravir particles are dispersed in a medium in which dolutegravir is not soluble (such as hexane, silicone or paraffine oil) and a suitable surfactant is added (such as DSSS (Dioctyl Sodium Sulfosuccinate)) to ensure proper dispersion of primary particles.

Figure 14:
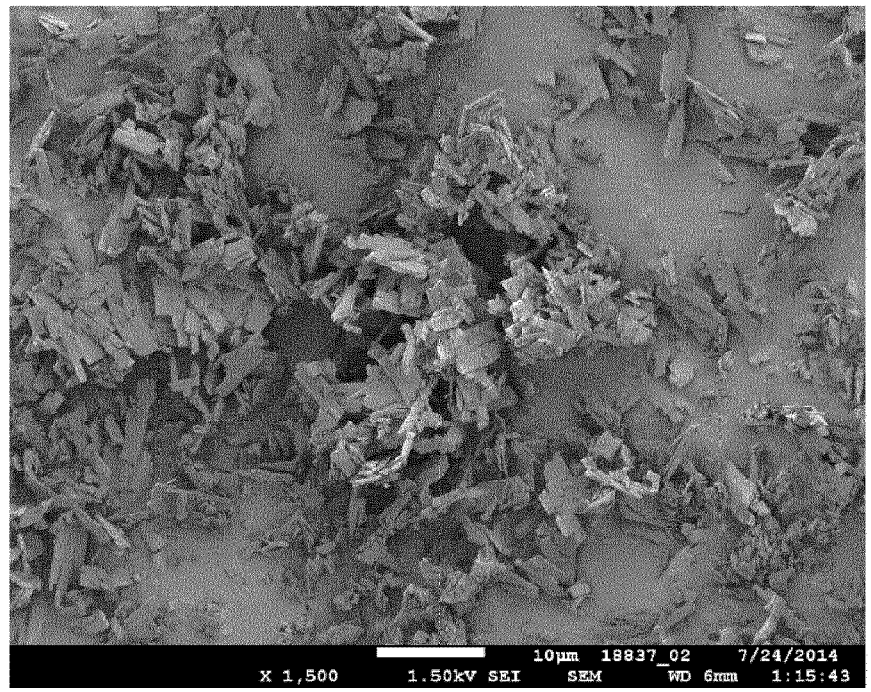
FIG. 14: Scanning electron micrograph images of crystalline dolutegravir Form HxA at 1.500× magnification (FIG. 14 a) and 5.000× magnification (FIG. 14 b)
Figure 14:
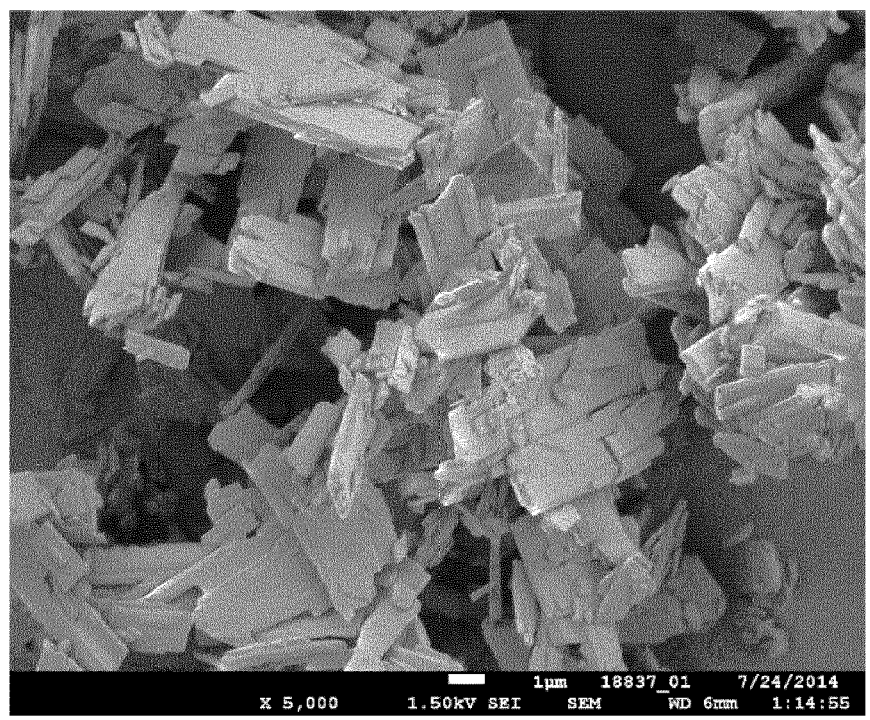

As shown in FIG. 14, form HxA has a thin-plate like morphology of primary particles. The crystal structure is layered with particle sizes of about 5 μm. The different external appearance of HxA is related to pseudo polymorphism.

This small size of the primary particles of crystals of form HxA is advantageous as it results in improved properties of form HxA, which, in turn, allows for improved formulation of dolutegravir (form HxA, respectively) in pharmaceutical compositions. For instance, in the currently marketed formulation of dolutegravir sodium (TIVICAY), it is necessary to carry out a micronization step (which is a size reduction step) in order to arrive at a mean volumetric particle size specification of d(0.9) below 10 μm. Such a small particle size is necessary in order to meet drug performance requirements, e.g. with regard to dissolution and/or bioavailability (see Regulatory Assessment Reports for Tivicay, e.g. EPAR or AUSPAR).

Surprisingly, already the primary particles of crystal form HxA can exhibit a mean volumetric PSD of below 10 μm. Therefore, it is not necessary to subject the obtained dolutegravir sodium particles to size reduction steps such as micronization (e.g. air jet milling), which is an example of a common and often used method for reducing API particle size. Subjecting API particles to size reduction processes can have negative impact, with regard to the API itself (such as negatively influencing physicochemical properties), the API's chemical and/or physical stability, but also with regard to formulation of the API: As size reduction steps can e.g. negatively impact flow and adhesion characteristics, applying simple formulation steps such as direct compression is difficult, if possible at all. Finally, carrying out a further processing step such as a size reduction step is time consuming, involves material loss and increases production costs. However, by providing the novel form HxA, a size reduction step can be omitted.

Furthermore, due to the superior properties of crystal form HxA, direct compression can be applied. This, in turn, may allow for applying an improved formulation process, e.g. in terms of cost and time, in particular when compared to alternative formulation steps such as wet granulation. Usually, wet granulation is applied in formulation processes in order to ensure homogeneity of the API, in particular when the API dosage per dosage form is comparably small, or to ensure proper flowability and compressibility of the tableting mixture. However, the novel crystalline form HxA exhibits superior, beneficial properties which make it possible that a wet granulation step can be omitted when formulating HxA.

Moreover, in another aspect the present invention relates to a novel hydrate of dolutegravir sodium, above and hereinafter also designated form Hy1B.

Form Hy1B is a monosodium salt of dolutegravir. Its molar ratio of dolutegravir and sodium typically and preferably lies in a range of about 1.0:0.9 to 1.1, more preferably of about 1.0:1.0.

Form Hy1B can be characterized by a PXRD comprising at least five peaks at 2-Theta angles selected from 6.3±0.2°, 7.4±0.2°, 10.9±0.2°, 11.1±0.2°, 12.7±0.2°, 16.2±0.2, 18.6±0.2°, 18.8±0.2°, 19.7±0.2°, 20.5±0.2°, 21.0±0.2°, 22.1±0.2°, 23.0±0.2°, 24.0±0.2°, 24.9±0.2° and/or 26.5±0.2°.

Preferably, form Hy1B is characterized by a PXRD comprising characteristic peaks at 2-Theta angles of 6.3±0.2°, 7.4±0.2°, 11.1±0.2°, 12.7±0.2° and 16.2±0.2°. Form Hy1B may be further characterized by a PXRD further comprising one or more additional characteristic peaks at 2-Theta angles of 10.9±0.2°, 18.6±0.2°, 18.8±0.2°, 19.7±0.2°, 20.5±0.2°, 21.0±0.2°, 22.1±0.2°, 23.0±0.2°, 24.0±0.2°, 24.9±0.2° and/or 26.5±0.2°. Preferably, form Hy1B may be further characterized by a PXRD further comprising one or more additional characteristic peaks at 2-Theta angles of 10.9±0.2°, 18.6±0.2°, 18.8±0.2°, 20.5±0.2°, 21.0±0.2° and/or 23.0±0.2°.

More preferably, form Hy1B is characterized by a PXRD comprising characteristic peaks at 2-Theta angles of 6.3±0.2°, 7.4±0.2°, 10.9±0.2°, 11.1±0.2°, 12.7±0.2°, 16.2±0.2°, 18.6±0.2°, 18.8±0.2°, 20.5±0.2°, 21.0±0.2° and 23.0±0.2°

Even more preferably, form Hy1B of a compound dolutegravir sodium is characterized by a powder X-ray diffractogram comprising characteristic peaks at 2-Theta angles of 6.3±0.2°, 7.4±0.2°, 10.9±0.2°, 11.1±0.2°, 12.7±0.2°, 16.2±0.2°, 18.6±0.2°, 18.8±0.2°, 19.7±0.2°, 20.5±0.2°, 21.0±0.2°, 22.1±0.2°, 23.0±0.2°, 24.0±0.2°, 24.9±0.2° and 26.5±0.2°.

XPRDs of form Hy1B according to the above aspect are measured preferably with Cu—Kα radiation, more preferably with Cu—Kα$_{1,2}$ radiation having a wavelength of 0.15419 nm at room temperature.

Figure 4:
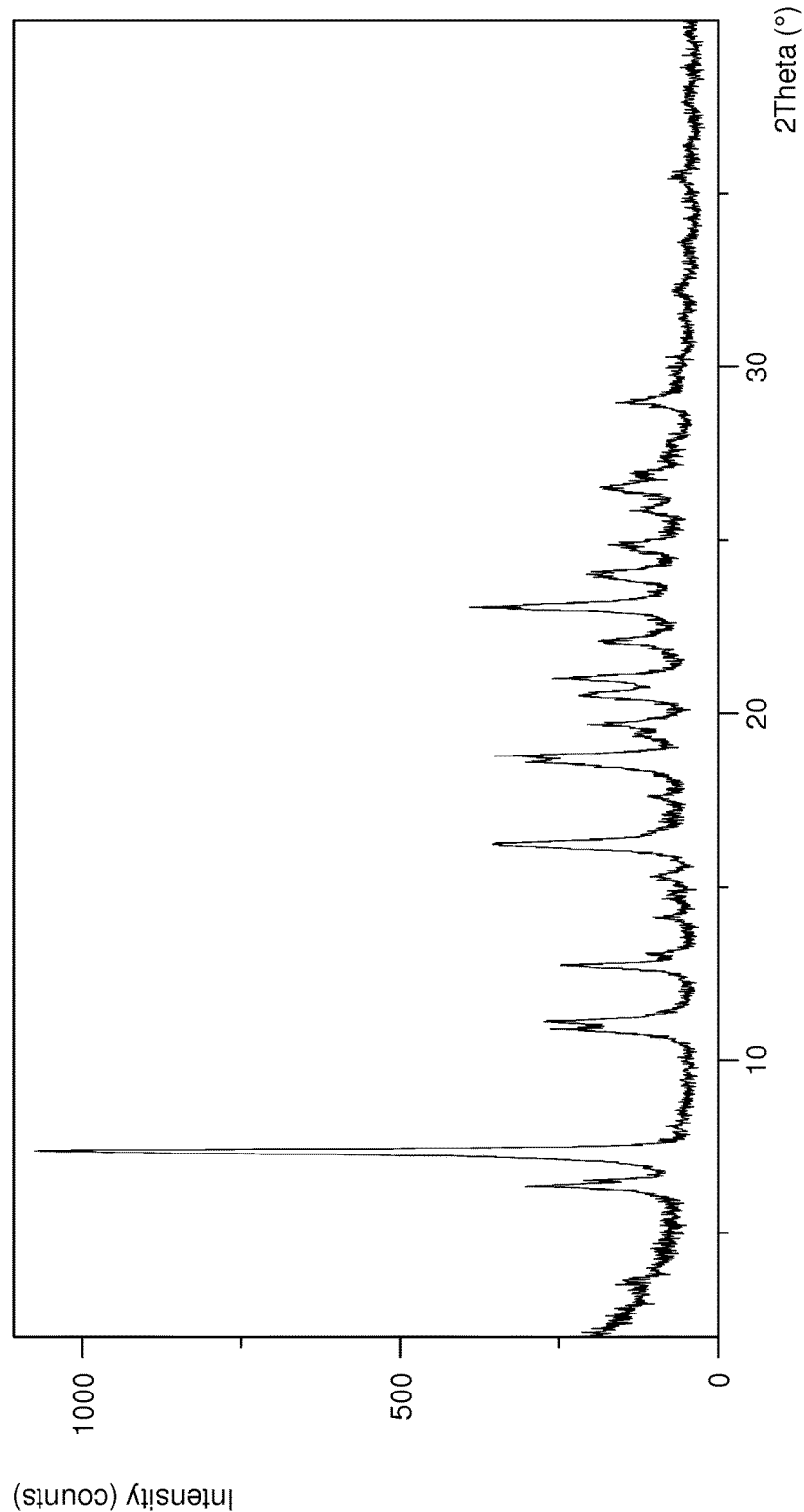
FIG. 4: Representative PXRD of dolutegravir sodium form Hy1B

A representative PXRD of form Hy1B is displayed in FIG. 4 herein. Additionally, form Hy1B can be characterized by showing a PXRD essentially the same as displayed in FIG. 4 when measured at room temperature with Cu—Kα$_{1,2}$ radiation having a wavelength of 0.15419 nm.

Figure 5:
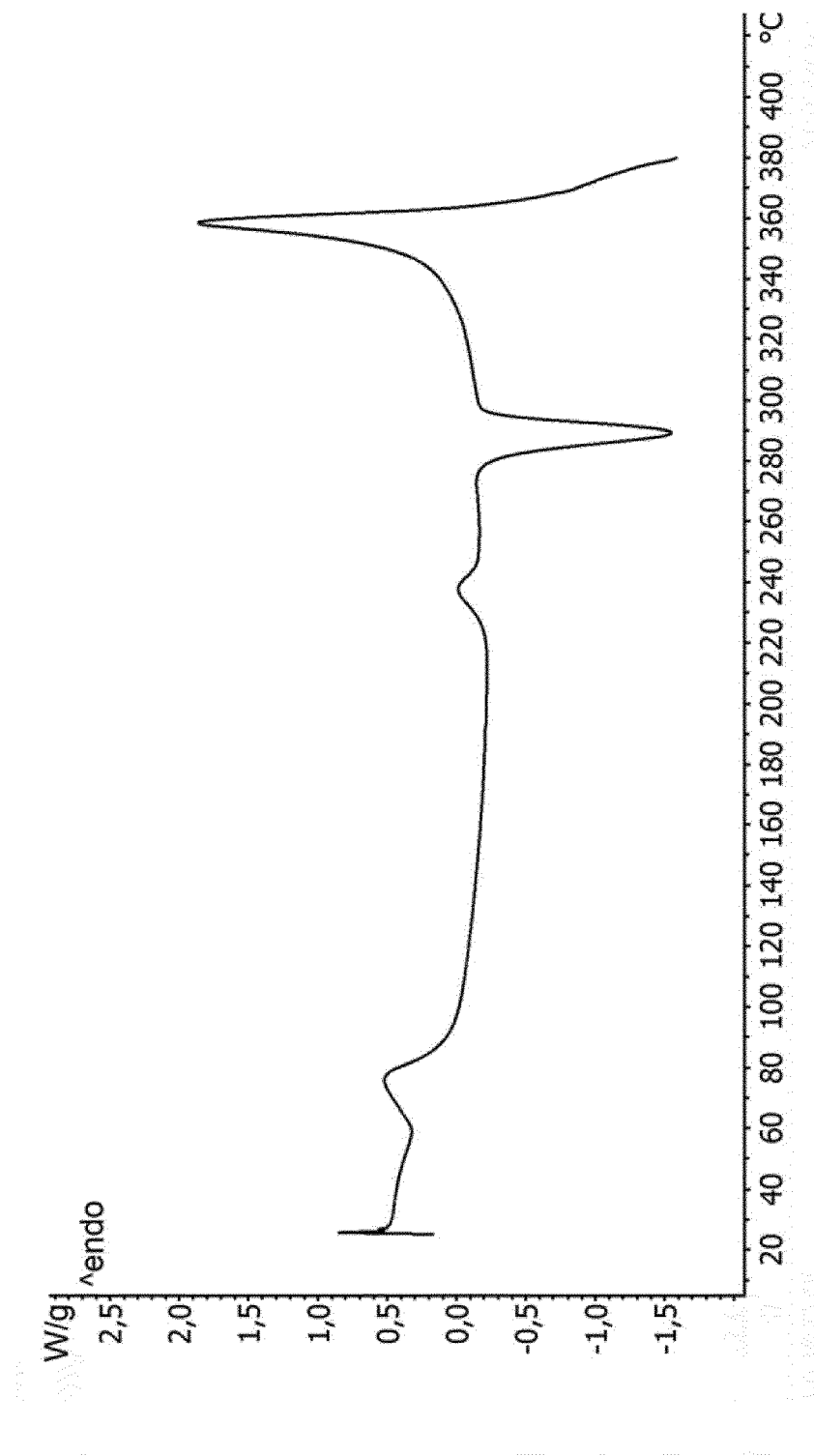
FIG. 5: Representative DSC curve of dolutegravir sodium form Hy1B equilibrated at about 30% RH and RT

Furthermore, a representative DSC curve of form Hy1B equilibrated at about 30% RH and RT is displayed in FIG. 5 herein. The DSC curve of form Hy1B shows a first endotherm at about 60 to 90° C. with a peak maximum at about 77° C., which is due to release of water. The second endotherm at about 220 to 250° C. with a peak maximum at about 237° C. is caused by melting. The exotherm, which occurs at about 275 to 300° C. and has a peak maximum at about 289° C. indicates that the anhydrous form of WO 2010/068253 A1 crystallizes from the melt. The final endotherm at about 340 to 370° C. with an onset temperature of about 350° C. and a peak maximum at about 358° C. is due to melting and decomposition respectively of the obtained anhydrous form of WO 2010/068253 A1.

Therefore, alternatively or additionally, form Hy1B can be characterized by a DSC curve comprising an endotherm at about 60 to 90° C. and/or an endotherm at about 220 to 250° C. when measured at a heating rate of 10° C./min. Form Hy1B can be further characterized by a DSC curve comprising an additional exotherm at about 275 to 300° C. when measured at a heating rate of 10° C./min.

Alternatively or additionally, form Hy1B can be characterized by melting in the range of about 220 to 250° C. when measured with DSC at a heating rate of 10° C./min.

Figure 6:
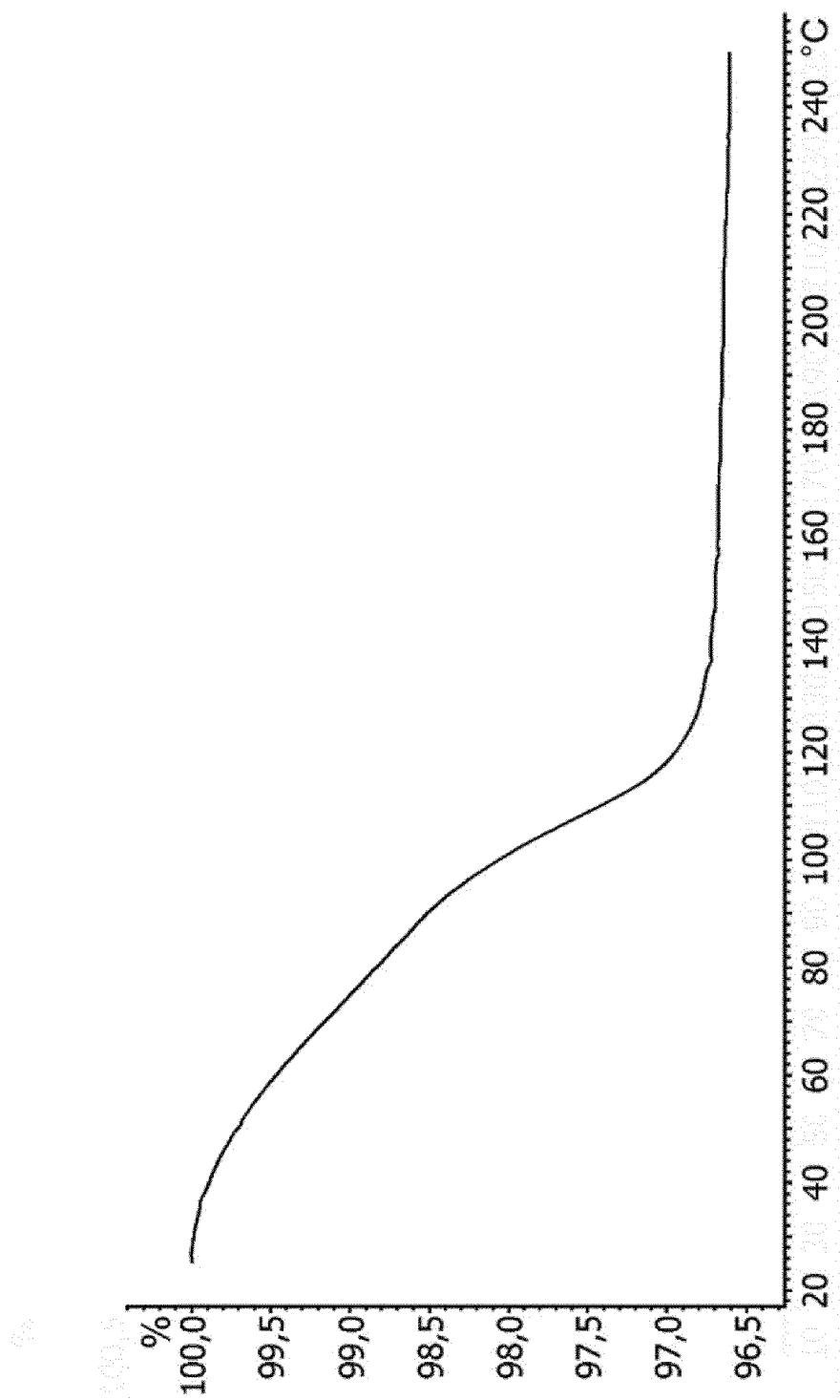
FIG. 6: Representative TGA curve of dolutegravir sodium form Hy1B equilibrated at about 30% RH and RT

In addition, a representative TGA curve of form Hy1B equilibrated at about 30% RH and RT is provided in FIG. 6 herein. The TGA curve of form Hy1B shows a weight loss of about 3.3% from 25 to 150° C. Coulometric Karl-Fischer titration of form Hy1B equilibrated at about 30% RH and RT revealed a water content of about 3.3% corresponding to 0.8 mol of water per mol of dolutegravir sodium. No organic solvent, in particular no ethanol was traceable by $^1$H-NMR.

Hence, alternatively or additionally, form Hy1B can be characterized by comprising not more than 0.5%, preferably not more than 0.4%, more preferably not more than 0.3% and most preferably not more than 0.2%, for example not more than 0.1% organic solvent. Alternatively or additionally, form Hy1B can be characterized by comprising not more than 0.5%, preferably not more than 0.4%, more preferably not more than 0.3% and most preferably not more than 0.2%, for example not more than 0.1% ethanol.

Figure 11:
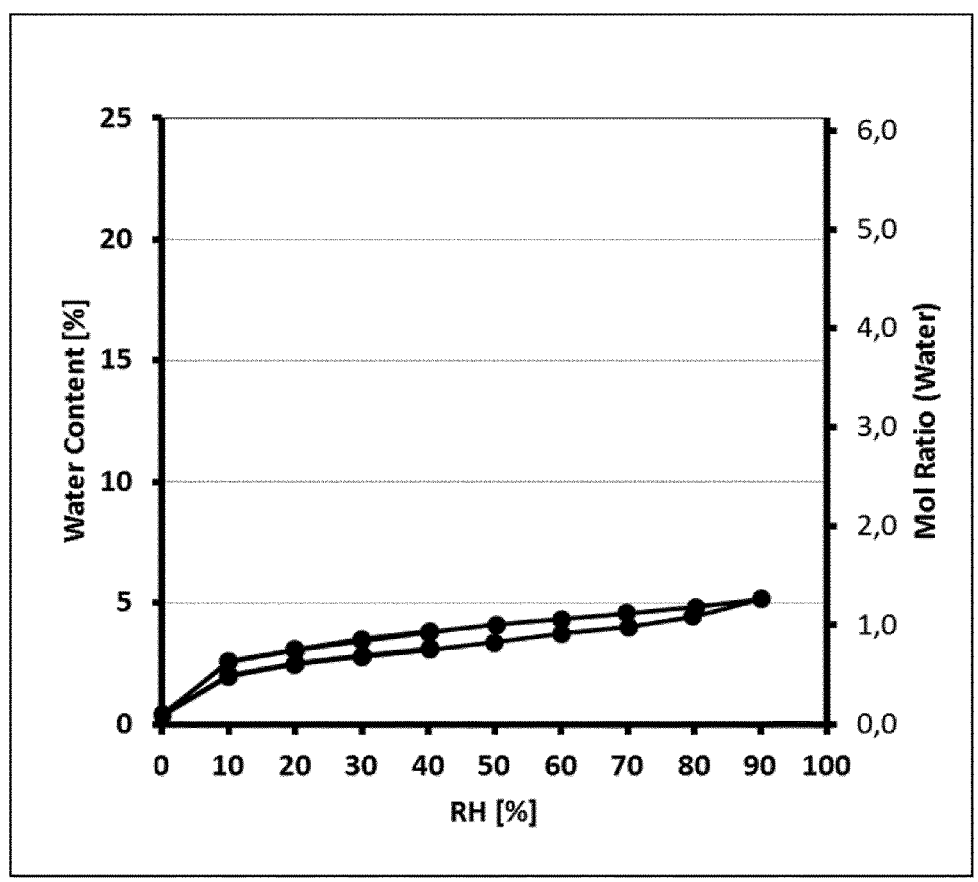
FIG. 11: Gravimetric moisture sorption/desorption isotherms of dolutegravir sodium form Hy1B

Representative gravimetric moisture sorption/desorption isotherms of form Hy1B are displayed in FIG. 11 herein. Form Hy1B, for example, shows a water content of about 2.8 to 3.5% corresponding to 0.7 to 0.9 mol of water per mol of dolutegravir sodium at about 30% RH and a water content of about 4.4 to 4.8% corresponding to 1.1 to 1.2 mol of water per mol of dolutegravir sodium at about 80% RH measured at temperature of 25±0.1° C. At 90% RH and 25±0.1° C. the sample shows a maximum water content of about 5.1% which corresponds to 1.3 mol of water per mol of dolutegravir sodium. According to GMSD experiments form Hy1B is a monohydrate.

Hence, alternatively or additionally, form Hy1B can be characterized as being a monohydrate of dolutegravir sodium.

Alternatively or additionally, form Hy1B can be characterized by comprising 0.7 to 1.3 mol of water per mol of dolutegravir sodium when measured at 30 to 90% RH and temperature of 25±0.1° C.

In a still further aspect the present invention relates to a process for the preparation of form Hy1B of dolutegravir sodium comprising subjecting dolutegravir sodium form $S_{EtOH/H2O}$ of the present invention to an atmosphere having a relative humidity of about at least 75±5% and a temperature of about at least 40° C.

The exact duration of the transformation from form $S_{EtOH/H2O}$ to form Hy1B may vary and mainly depends on parameters like sample amount, thickness of the powder layer, particle size, and specific surface area. Usually, the transformation is complete in about 12 to 168 hours, preferably in about 12 to 120 hours, more preferably in about 12 to 72 hours and most preferably the transformation is complete in about 12 to 24 hours.

In a still further aspect the present invention relates to a novel crystalline form of dolutegravir sodium, above and hereinafter also designated form $S_{EtOH/H2O}$.

Form $S_{EtOH/H2O}$ is a monosodium salt of dolutegravir. Its molar ratio of dolutegravir and sodium typically and preferably lies in the range of about 1.0:0.9 to 1.1, preferably of about 1.0:1.0.

Form $S_{EtOH/H2O}$ can be characterized by a PXRD comprising at least five peaks at 2-Theta angles selected from 6.5±0.2°, 7.0±0.2°, 10.6±0.2°, 11.0±0.2°, 13.3±0.2°, 16.0±0.2°, 18.0±0.2°, 19.1±0.2°, 20.3±0.2°, 20.8±0.2° and/or 22.6±0.2°.

Preferably, form $S_{EtOH/H2O}$ is characterized by a PXRD comprising characteristic peaks at 2-Theta angles of 6.5±0.2°, 7.0±0.2°, 13.3±0.2°, 16.0±0.2° and 22.6±0.2°. Form $S_{EtOH/H2O}$ may be further characterized by a PXRD further comprising one or more additional characteristic peaks at 2-Theta angles of 10.6±0.2°, 11.0±0.2°, 18.0±0.2°, 19.1±0.2°, 20.3±0.2° and/or 20.8±0.2°. Preferably, form $S_{EtOH/H2O}$ may be further characterized by a PXRD further comprising one or more additional characteristic peaks at 2-Theta angles of 10.6±0.2°, 11.0±0.2°, 18.0±0.2°, 19.1±0.2° and/or 20.3±0.2°.

More preferably, form $S_{EtOH/H2O}$ is characterized by a PXRD comprising characteristic peaks at 2-Theta angles of 6.5±0.2°, 7.0±0.2°, 10.6±0.2°, 11.0±0.2°, 13.3±0.2°, 16.0±0.2°, 18.0±0.2°, 19.1±0.2°, 20.3±0.2° and 22.6±0.2°.

Even more preferably, form $S_{EtOH/H2O}$ is characterized by a PXRD comprising characteristic peaks at 2-Theta angles of 6.5±0.2°, 7.0±0.2°, 10.6±0.2°, 11.0±0.2°, 13.3±0.2°, 16.0±0.2°, 18.0±0.2°, 19.1±0.2°, 20.3±0.2°, 20.8±0.2° and 22.6±0.2°, XPRDs of form $S_{EtOH/H2O}$ according to the above alternatives are measured preferably with Cu—Kα radiation, more preferably with Cu—Kα$_{1,2}$ radiation having a wavelength of 0.15419 nm at room temperature.

Figure 7:
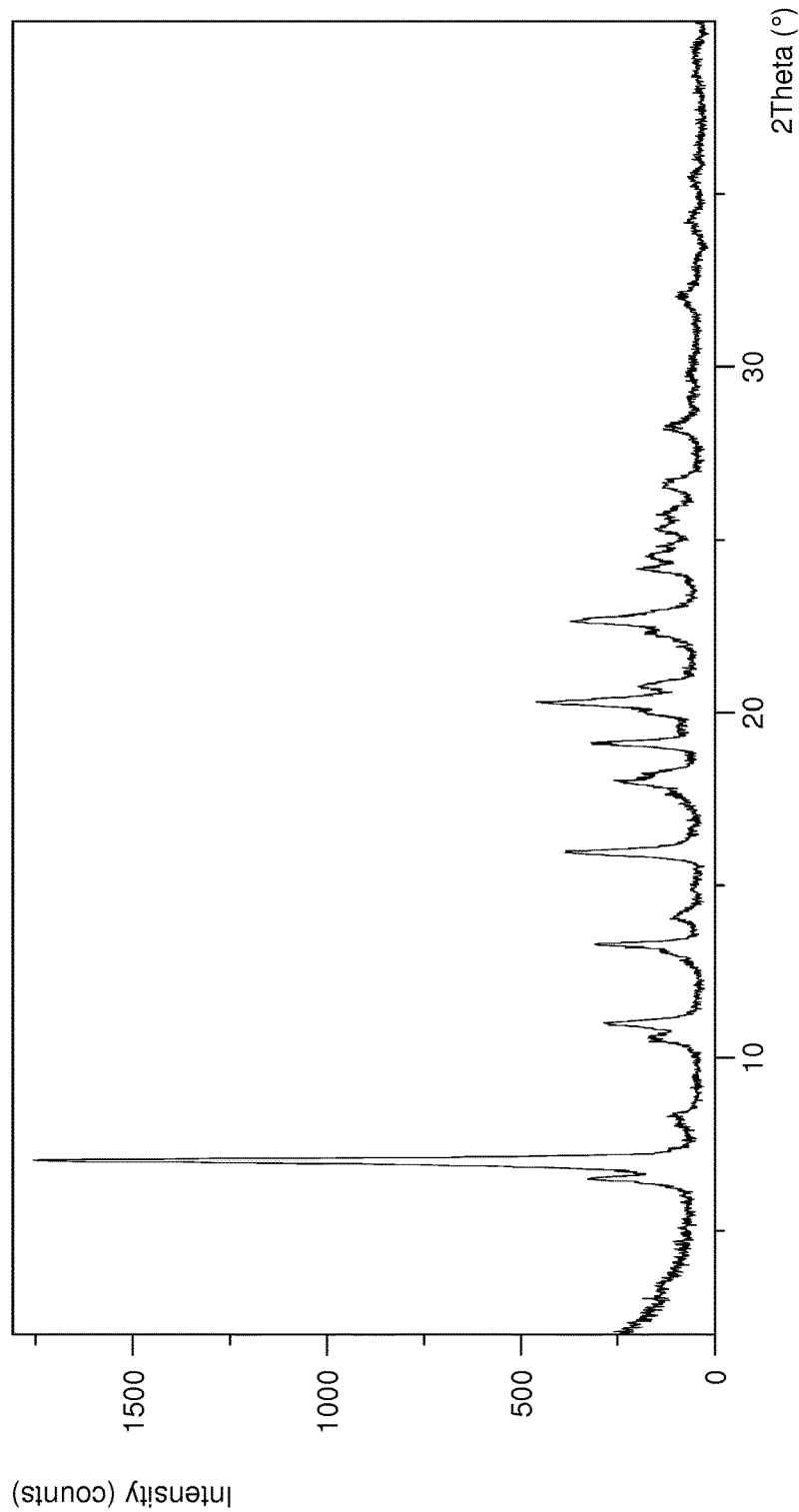
FIG. 7: Representative PXRD of dolutegravir sodium form $S_{EtOH/H2O}$

A representative PXRD of form $S_{EtOH/H2O}$ is displayed in FIG. 7 herein. Additionally, form $S_{EtOH/H2O}$ can be characterized by showing a PXRD essentially the same as displayed in FIG. 7 when measured at room temperature with Cu—K$\alpha_{1,2}$ radiation having a wavelength of 0.15419 nm.

Figure 8:
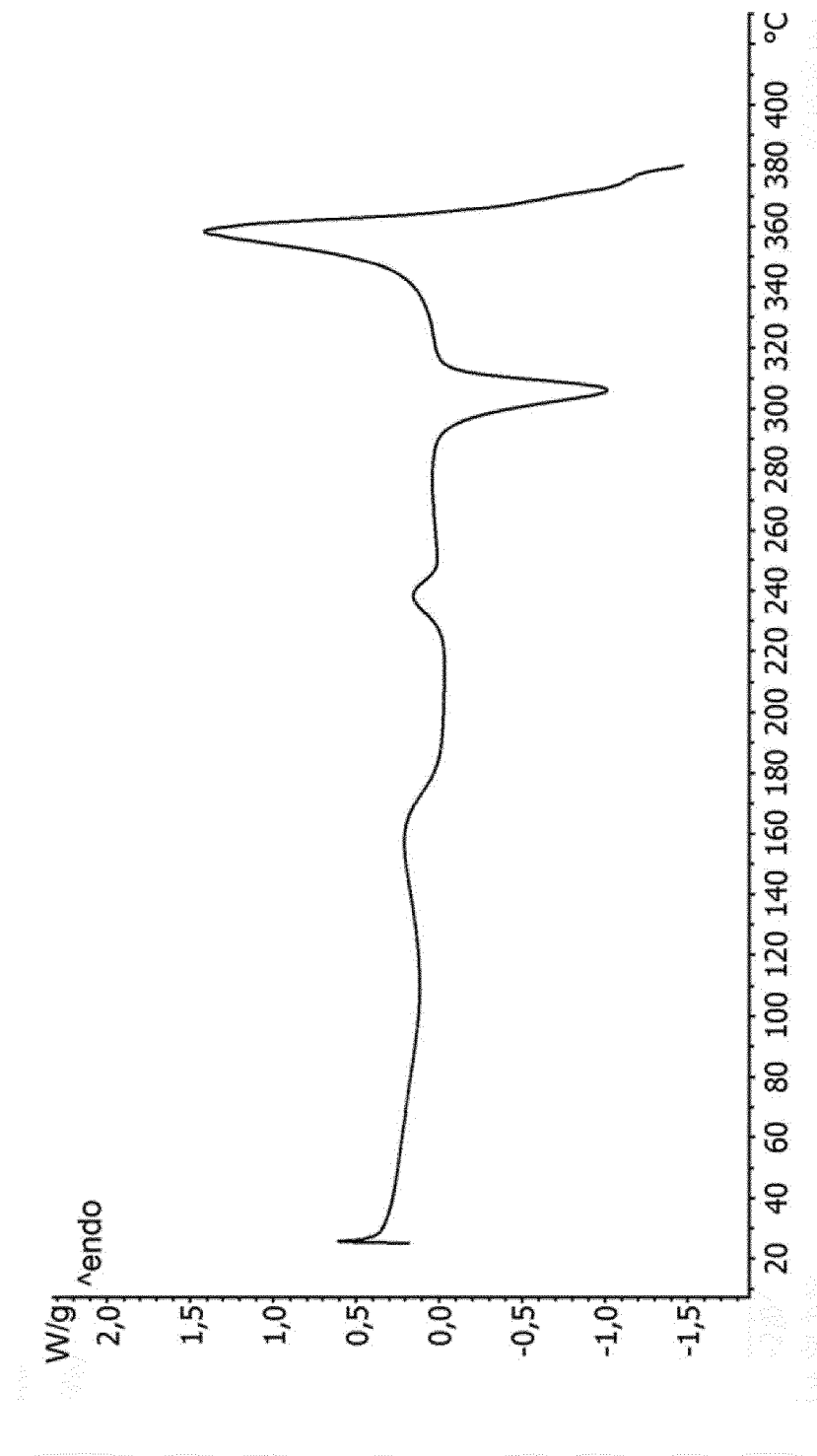
FIG. 8: Representative DSC curve of dolutegravir sodium form $S_{EtOH/H2O}$ equilibrated at about 25% RH and RT

Furthermore, a representative DSC curve of form $S_{EtOH/H2O}$ equilibrated at about 25% RH and RT is displayed in FIG. 8 herein. The DSC curve of form $S_{EtOH/H2O}$ shows a first endotherm at about 110 to 185° C. with a peak maximum at about 159° C., which is due to release of ethanol and water respectively. The second endotherm at about 220 to 250° C. with a peak maximum at about 238° C. is caused by melting. The exotherm, which occurs at about 285 to 320° C. and has a peak maximum at about 306° C. indicates that the anhydrous form of WO 2010/068253 A1 crystallizes from the melt. The final endotherm at about 340 to 370° C. with an onset temperature of about 350° C. and a peak maximum at about 358° C. is due to melting and decomposition respectively of the obtained anhydrous form of WO 2010/068253 A1.

Therefore, alternatively or additionally, form $S_{EtOH/H2O}$ can be characterized by a DSC curve comprising an endotherm at about 110 to 185° C. and/or an endotherm at about 220 to 250° C. when measured at a heating rate of 10° C./min. Form $S_{EtOH/H2O}$ can be further characterized by a DSC curve comprising an additional exotherm at about 285 to 320° C. when measured at a heating rate of 10° C./min.

Alternatively or additionally, form $S_{EtOH/H2O}$ can be characterized by melting in the range of about 220 to 250° C. when measured with DSC at a heating rate of 10° C./min.

Figure 9:
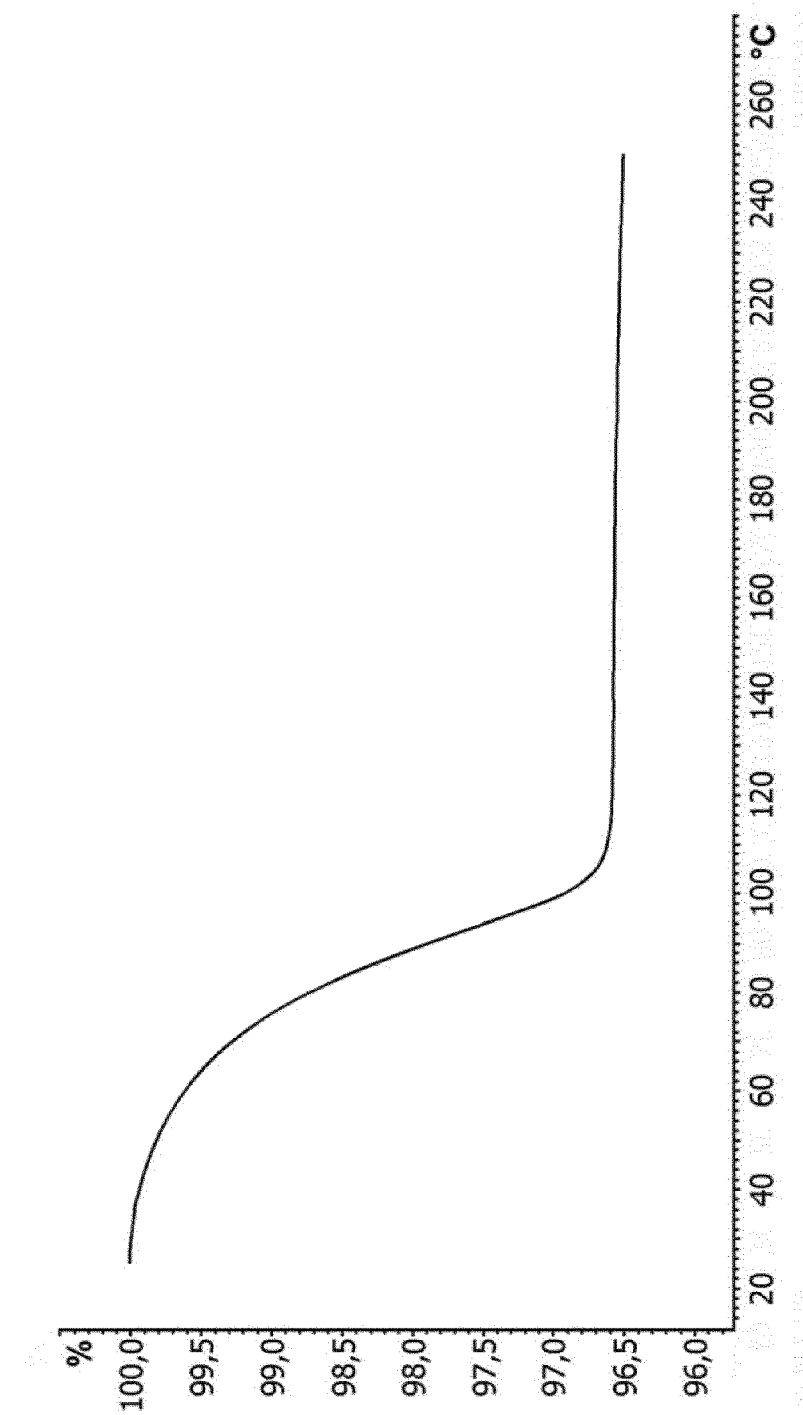
FIG. 9: Representative TGA curve of dolutegravir sodium form $S_{EtOH/H2O}$ equilibrated at about 25% RH and RT

In addition, a representative TGA curve of form $S_{EtOH/H2O}$ equilibrated at about 25% RH and RT is provided in FIG. 9 herein. The TGA curve of form $S_{EtOH/H2O}$ shows a weight loss of about 3.4% from 25 to 120° C. Coulometric Karl-Fischer titration of form $S_{EtOH/H2O}$ equilibrated at about 25% RH and room temperature revealed a water content of about 0.9% corresponding to 0.2 mol of water per mol of dolutegravir sodium. Ethanol was detectable by $^1$H-NMR. Combining the results from TGA, Karl-Fischer titration and $^1$H-NMR it can be concluded that form $S_{EtOH/H2O}$ comprises about 2.5% ethanol corresponding to 0.3 mol of ethanol per mol of dolutegravir sodium and about 0.9% water corresponding to 0.2 mol of water per mol of dolutegravir sodium when measured at about 25% RH and RT.

Hence, alternatively or additionally, form $S_{EtOH/H2O}$ can be characterized as being an ethanolate/hydrate of dolutegravir sodium.

Alternatively or additionally, form $S_{EtOH/H2O}$ can be characterized by comprising 0.3 mol of ethanol and 0.2 mol of water per mol of dolutegravir sodium when measured at about 25% RH and room temperature.

In a still further aspect the present invention relates to a process for the preparation of form $S_{EtOH/H2O}$ of dolutegravir sodium comprising the steps of:
  (i) providing a suspension or a solution of dolutegravir in a solvent comprising at least 90 volume % ethanol
  (ii) reacting dolutegravir with sodium ethoxide at a temperature of not more than 45° C. and
  (iii) precipitating dolutegravir sodium.

Dolutegravir, which is used as starting material for form $S_{EtOH/H2O}$ production can be prepared in accordance with the procedures disclosed in examples 1a to 1k or 3a to 3k of WO 2010/068253 A1.

In a first step, a suspension or a solution of dolutegravir in a solvent comprising ethanol is prepared. Preferably, the ethanol concentration of the solvent used for preparing the mixture is about at least 90 volume %, more preferably about at least 96 volume % and most preferably about at least 99 volume %. Moreover, the water content of the solvent preferably is about not more than 10 volume %, more preferably about not more than 4 volume % and most preferably about not more than 1 volume %.

The initial suspension or solution applied comprises about 10 to 100 g dolutegravir per liter solvent, preferably about 10 to 75 g, more preferably about 10 to 50 g and most preferably about 10 to 25 g dolutegravir per liter solvent are employed.

In the next step dolutegravir is reacted with sodium ethoxide by adding sodium ethoxide to the mixture or vice versa. Sodium ethoxide may be applied as solid or ethanolic solution, whereat solutions which may be applied in the present process have a concentration of about 1 to 25 weight %, preferably of about 10 to 21 weight %, more preferably of about 15-21 weight % and most preferably of about 21 weight %. The ratio of dolutegravir and sodium ethoxide employed is about 1.0:0.8 to 2.0, preferably about 1.0:0.9 to 1.5, more preferably about 1.0:0.9 to 1.2 and most preferably a 1.0:1.0 ratio is used.

Essentially, when combining sodium ethoxide and dolutegravir, the reaction temperature is kept at about not more than 45° C., preferably at about not more than 40° C., more preferably at about not more than 35° C. and most preferably at about not more than 30° C. The suspension or the solution is kept at the applied temperature for about 1 to 24 hours, preferably for about 1 to 12 hours, more preferably for about 1 to 6 hours and most preferably for about 1 to 2 hours, preferably under stirring.

Subsequently, at least a portion of the obtained dolutegravir sodium may be collected by any conventional method such as filtration or centrifugation, preferably by filtration.

Finally, the isolated dolutegravir sodium crystals may be dried at a temperature of about not more than 80° C., preferably of about not more than 60° C., more preferably of about not more than 50° C. and most preferably the crystals are dried at a temperature of about not more than 40° C. for example at about room temperature. Drying may be performed for about 1 to 72 hours, preferably for about 2 to 48 hours, more preferably for about 4 to 24 hours and most preferably for about 6 to 18 hours. Drying may be performed under vacuum preferably at about not more than 100 mbar, more preferably at about not more than 50 mbar and most preferably at about not more than 30 mbar, for example at about 20 to 30 mbar.

Having form $S_{EtOH/H2O}$ in hands, for the first time allows the preparation of the novel monohydrate Hy1B of the present invention. Form Hy1B can be prepared by subjecting the form $S_{EtOH/H2O}$ crystals to elevated humidity and temperature. Therefore, form $S_{EtOH/H2O}$ is a valuable intermediate for the preparation of form Hy1B of the present invention.

Hence, in an eighth aspect the present invention relates to the use of dolutegravir sodium form $S_{EtOH/H2O}$ for the preparation of dolutegravir sodium form Hy1B.

WO 2010/068253 A1 discloses a monohydrate of dolutegravir sodium from which the non-stoichiometric hydrate HxA of the present invention can for example be differentiated by comprising PXRD peaks at 12.5 and 20.8±0.2° 2-Theta, whereas the known monohydrate does not show significant peaks in this area. On the other hand the monohydrate Hy1B of the present invention differs from the monohydrate disclosed in WO 2010/068253 A1 for example by comprising PXRD peaks at 6.3 and 7.4±0.2° 2-Theta, whereas the known monohydrate does not show significant peaks in this area. Instead, the monohydrate of WO 2010/068253 A1 shows for example PXRD peaks at 8.0 and 9.3±0.2° 2-Theta, whereas the monohydrate Hy1B of the present invention shows no peaks in this area.

Figure 12:
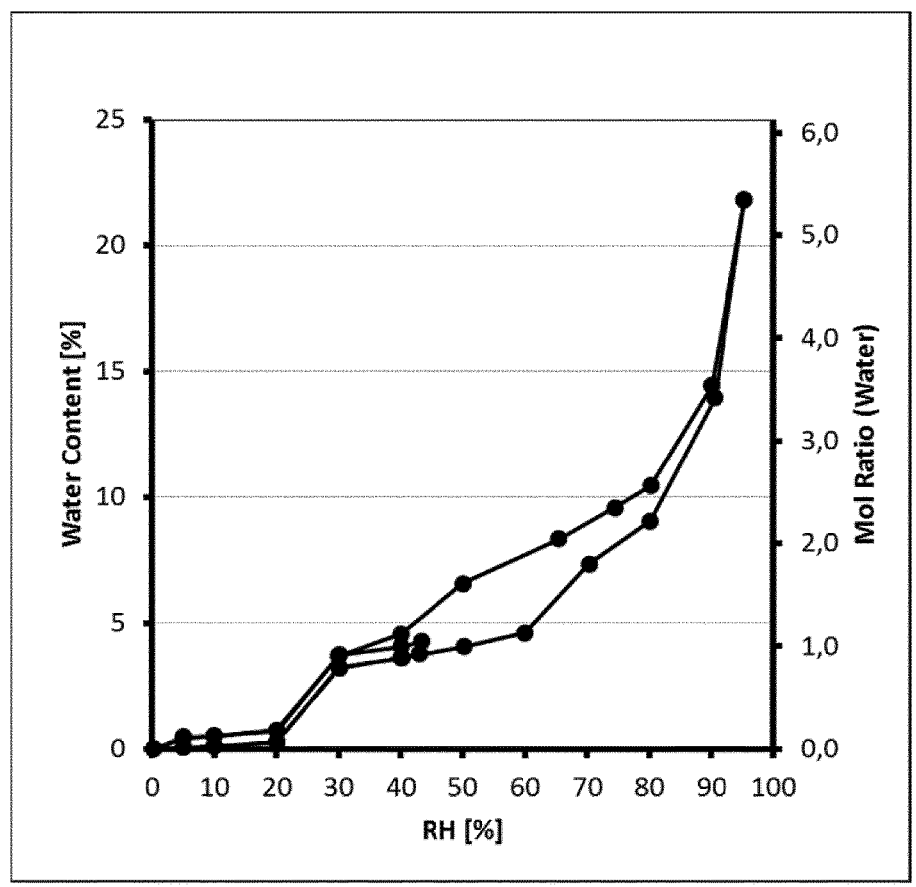
FIG. 12: Gravimetric moisture sorption/desorption isotherms of dolutegravir sodium monohydrate of WO 2010/068253 A1

Comparative gravimetric moisture sorption/desorption experiments at 25±0.1° C. were conducted with dolutegravir sodium monohydrate of WO 2010/068253 A1 and the hydrates of the present invention designated form HxA and form Hy1B. The resulting sorption/desorption isotherms of the monohydrate of WO 2010/068253 A1 are displayed in FIG. 12, whereat the isotherms of the non-stoichiometric hydrate HxA and the monohydrate Hy1B of the present invention are disclosed in FIGS. 10 and 11 respectively.

Below 30% RH dolutegravir sodium monohydrate of WO 2010/068253 A1 shows reversible dehydration to an anhydrous form. On the other hand, above 60% relative humidity the monohydrate excessively takes up water until a water content of about 21.8% is reached at 95% RH, which corresponds to 5.6 mol of water per mol of dolutegravir sodium. Although, this water uptake is reversible when humidity is decreased, the hysteresis between the sorption and desorption isotherms in the area from about 40 to 90% RH indicates significant structural changes. Therefore, it can be concluded that dolutegravir sodium monohydrate of WO 2010/068253 A1 is very hygroscopic and preserves its crystal structure only within a narrow window of 30 to 60% RH.

On the contrary, form HxA of the present invention only shows slight water uptake in the sorption cycle until a water content of 3.9% is reached at 95% RH. The water uptake during the sorption cycle is reversible when humidity is decreased. The absence of a hysteresis between the sorption and desorption isotherms indicates that the crystal structure remains stable during the whole experiment, which was confirmed by moisture dependent PXRD. In summary, dolutegravir sodium form HxA of the present invention is stable and preserves its crystal structure from about 0 to 95% RH and is significantly less hygroscopic than the monohydrate of WO 2010/068253 A1.

Form Hy1B also shows only slight water uptake in the sorption cycle until a water content of 5.1% is reached at 90% RH. The water uptake is reversible when humidity is decreased. The absence of a significant hysteresis between the sorption and desorption isotherms indicates that the crystal structure remains stable between 10 to 90% RH, which was confirmed by moisture dependent PXRD. Only below 10% RH reversible dehydration to an anhydrous form of dolutegravir sodium can be observed. Therefore, dolutegravir sodium form Hy1B of the present invention is stable and preserves its crystal structure from 10 to 90% RH and is significantly less hygroscopic than the monohydrate of WO 2010/068253 A1.

The results of the GMSD experiments are again summarized in table 1 below:

TABLE 1

Summary of the results from comparative GMSD experiments

| | Δm sorption [0-90% RH] | Δm sorption [30-90% RH] | Remarks |
|---|---|---|---|
| Form HxA | +3.4% | +2.5% | stable at 0-95% RH, no structural changes observed, no significant hysterises |
| Form Hy1B | +4.8% | +2.4% | stable at 10-90% RH, dehydration below 10% RH, no significant hysterises |
| MH of WO 2010/068253 | +14.0% | +10.7% | stable at 30-60% RH, dehydration below 30% RH, hysterises at 40-95% RH |

Hence, scope of the present invention was the provision of novel hydrates of dolutegravir sodium which absorb only low amounts of water when subjected to moisture and preserve their crystal structure at wet and dry conditions. Due to their superior properties, the hydrates of the present invention can be easily formulated as well as packaged and stored in a controlled way.

Therefore, in a further aspect the present invention relates to the use of dolutegravir sodium form HxA and/or form Hy1B for the preparation of pharmaceutical compositions.

In addition, the present invention relates to pharmaceutical compositions comprising an effective amount of dolutegravir sodium form HxA and/or form Hy1B and at least one pharmaceutically acceptable excipient.

The solid pharmaceutical dosage form may comprise one or more further pharmaceutically acceptable excipients, such as e.g. diluents/fillers, binder, disintegrants, glidants, surfactants and flow regulators ("Lexikon der Hilfsstoffe fur Pharmazie, Kosmetik and angrenzende Gebiete", edited by H. P. Fiedler, 5th Edition, and "Handbook of Pharmaceutical Excipients", 6th Edition, edited by Arthur H. Kibbe, American Pharmaceutical Association, Washington, USA, and Pharmaceutical Press, London).

Preferably, the pharmaceutical composition comprises dolutegravir sodium form HxA, and one or more pharmaceutically acceptable excipients selected from the group consisting of diluent/filler, binder, disintegrant, lubricant, and surfactant. In a preferred embodiment, the diluent/filler is selected from the group consisting of sugar, cellulose or a derivative thereof, starch, calcium phosphate, calcium or magnesium carbonat, and mixtures thereof, preferably, the diluent/filler is microcrystalline cellulose and/or D-mannitol; the binder is selected from the group consisting of povidone, tragacanth, sodium alginate, gum arabic, starch pregelatinized, gelatin and cellulosic derivates, preferably the binder is povidone; the disintegrant is selected from the group consisting of croscarmellose sodium, sodium carboxymethyl starch, cross-linked polyvinylpyrrolidone, sodium carboxymethyl glycolate, sodium starch glycolate, low-substituted hydroxypropyl cellulose, citric acid and sodium bicarbonate, preferably the disintegrant is sodium starch glycolate; the lubricant is selected from the group consisting of colloidal silicon dioxide (such as Aerosil®), talc, stearic acid, magnesium stearate, calcium stearate, zinc sterate, glyceryl behenate, sodium stearyl fumarate, polyethylene glycol, and silicon dioxide, preferably the lubricant is sodium stearyl fumarate; the surfactant is selected from the group consisting of tween such as tween 80, polyoxyethylene-polyoxypropylene copolymer and sodium lauryl sulfate, preferably the surfactant is sodium lauryl sulfate. Preferably, the pharmaceutical composition can further comprise at least one glidant selected from magnesium stearate, Aerosil® (colloidal silicon dioxide), starch and talc.

In a further preferred embodiment, the dolutegravir sodium form HxA is present in an amount of from 5% to 30%, preferably of from 10% to 25%, more preferably of from 12% to 20%, and most preferably of from 15% to 19% by weight of the total weight of the pharmaceutical composition without coating, if present; the diluent/filler is present in the pharmaceutical composition in an amount of from 0 to 90% by weight, preferably of from 20% to 80% by weight, more preferably of from 40% to 70% by weight, and most preferably of from 50% to 70% by weight of the total weight of the pharmaceutical composition without coating, if present; the binder is present in the pharmaceutical composition in an amount of from 0 to 40% by weight, preferably of from 1% to 20% by weight, more preferably of from 2% to 10% by weight, and most preferably of from 3% to 8% by weight of the total weight of the pharmaceutical composition without coating, if present; the disintegrant is present in the pharmaceutical composition in an amount of from 0 to 40% by weight, preferably of from 1% to 20% by weight, more preferably of from 2% to 10% by weight, and most preferably of from 3% to 8% by weight of the total weight of the pharmaceutical composition without coating, if present; the lubricant is present in the pharmaceutical composition in an amount of from 0 to 10% by weight, preferably of from 0.1% to 8% by weight, more preferably of from 1% to 5% by weight, and most preferably of from 1% to 3% by weight of the total weight of the pharmaceutical composition without coating, if present; the surfactant is present in the pharmaceutical composition in an amount of from 0 to 5% by weight, preferably of from 0.5% to 4% by weight, more preferably of from 1% to 3% by weight, and most preferably of from 1% to 2% by weight of the total weight of the pharmaceutical composition without coating, if present.

Particularly preferred, the (preferably only) pharmaceutically acceptable excipients that are present in said pharmaceutical composition are at least one filler/diluent, preferably mannitol, more preferably D-mannitol, and/or microcrystalline cellulose; a binder, preferably povidone such as Plasodone K29/32; a disintegrant, preferably sodium starch glycolate such as Primojel; and a lubricant, preferably sodium stearyl fumarate; wherein the respective excipients are different from each other. Thus, an example of such a particularly preferred pharmaceutical composition is a composition that, in addition to the crystalline form HxA sodium, comprises, preferably consists of, D-mannitol, micrycrystalline cellulose, povidone, sodium starch glycolate, and sodium starch fumarate as pharmaceutically acceptable excipients. It is not excluded that this pharmaceutical composition comprises one or more outer layer(s) such as coating(s).

The pharmaceutical composition can be present in the form of an oral dosage form, preferably in form of a solid oral dosage form such as a capsule, tablet, pellet, or sachet. More preferably, the pharmaceutical composition is present in form of a tablet.

Upon carrying out suitable dissolution tests, it can be seen that the oral dosage form, preferably the tablet, comprising crystalline form HxA and the pharmaceutically acceptable excipients, exhibits a dissolution profile that fulfills regulatory drug performance requirements of immediate release tablets, as for instance regulated in the FDA Guidance for Industry (Dissolution Testing of Immediate Release Solid Oral Dosage Forms). A suitable dissolution test that has been carried out in the present invention is the dissolution testing applying the "US paddle Apparatus 2", which is a standardized apparatus and specified in the United States Pharmacopoeia General Chapter <711> Dissolution. As can be seen from example 15, table 12, after 45 minutes at least 75% of the crystalline form HxA is dissolved. Thus, preferrably, at least 75% of the crystalline form HxA of the total amount of the crystalline form HxA present in the dosage form are dissolved in 45 minutes or less when measured using USP paddle Apparatus 2 at 50 rpm in 0.9% NaCl, pH 6.8 phosphate buffer, and water.

As could further be shown in the present invention, the content uniformity of solid dosage forms comprising the crystalline form HxA is improved compared to reference form "Form I" (table 13). This is all the more surprising and advantageous, as the solid oral dosage form comprising Form I was prepared by wet granulation (due to technical reasons direct compression was not possible; cf. explanation with this regard in Example 14 below), whereas the solid oral dosage form comprising form HxA was prepared by direct compression. Usually, wet granulation is applied amongst others in order to facilitate and ensure a proper homogeneity. However, the properties of a solid dosage form comprising form HxA are superior compared to form I which is used in the marketed form (TIVICAY) e.g. with regard to content uniformity.

Also with regard to stress stability, a dosage form comprising form HxA exhibited excellent chemical stability (cf. example 15, table 14).

The present invention further refers to a process for preparing a pharmaceutical composition comprising form HxA, comprising the steps of:
(I) providing the crystalline form HxA;
(II) mixing the crystalline form HxA with the pharmaceutical excipients as defined above in connection with the pharmaceutical composition comprising form HxA;
(III) obtaining the pharmaceutical composition.

In a preferred embodiment, step (II) comprises:
(II-1) mixing together form HxA, which preferably is prepared according to the process defined herein, and at least one diluent/filler;
(II-2) sieving the obtained mixture of step (II-1) through an appropriate mesh size, preferably through a mesh sieve of from 0.5 mm to 2.0 mm, more preferably of 0.7 mm
(II-3) adding binder and disintegtant;
(II-4) mixing the mixture of step (II-3);
(II-5) adding sieved lubricant; and
(II-6) blending the mixture of step (II-5).

The present invention further refers to a process for preparing oral dosage forms, comprising the steps of:
  (i) providing the crystalline form HxA, and the pharmaceutical excipients as disclosed above;
  (ii) formulating the crystalline form HxA and the pharmaceutically acceptable excipients of step (i) into an oral dosage form, preferably without using a wet granulation step in step (ii), more preferably without using a granulation step at all; even more preferably step (ii) comprises a direct compression process;
  (iii) obtaining said oral dosage form.

In a first step, crystalline form HxA and at least one diluent/filler are mixed together and sieved through an appropriate sieve size (i.e. a mesh sieve of from 0.5 mm to 2.0 mm, more preferably of 0.7 mm). This sieving step is used to eliminate light agglomerates of bigger size (for example 1-2 cm) that might be formed during API/excipient storage (also called delumping step). The primary particles size is not affected by this step. Then, binder and disintegrant can be added and further mixed. Then, sieved lubricant (sieved through an appropriate mesh size, such as 0.5 mm) can be added and the resulting mixture can additionally be blended. Preferably, the at least one diluent/filler, binder and disintegrant are as defined above in connection with the pharmaceutical composition comprising crystalline form HxA.

In a next step, the resulting blend, obtained after step (i), is formulated into an oral dosage form (step (ii)). This step can be carried out by any suitable method that is known to a person skilled in the art, however in an advantageous embodiment wet granulation is excluded. Step (ii) can comprises direct compression or dry granulation, preferably step (ii) comprises direct compression. In a more preferred embodiment, step (ii) is direct compression. The formulating step (ii) can be carried out according to any suitable protocol that is known to a person skilled in the art. Preferably, step (ii) is carried out by using any suitable tableting machine that is known to a person skilled in the art. For instance, direct compression can be carried out by using a rotary tableting machine, and the tableting punch used is a round 10 mm punch. However, any suitable tableting punch can be used. After having carried out step (ii), the oral dosage form (preferably, a tablet) is obtained.

It is also possible that in a further step (iv) a coating is applied onto the oral dosage form obtained after step (iii), preferably resulting in a film coated tablet.

In a preferred embodiment, the process for preparing oral dosage forms according to the present invention does not include, preferably neither include nor require, a size reduction step of the crystalline form HxA. This is because the mean volume PSD of the crystalline form HxA is already small enough to make further processing such as formulating into dosage froms possible, while at the same time providing crystalline form HxA that exhibits at least sufficiently good, preferably improved, properties e.g. with regard to formulation.

In a further preferred embodiment, the crystalline form HxA is prepared as disclosed in the present invention.

Finally, the present invention relates to pharmaceutical compositions or dosage forms, as disclosed herein, comprising an effective amount of dolutegravir sodium form HxA and/or form Hy1B for use in the treatment of human immunodefiency virus type 1 (HIV-1) infection.

An infiltration by the human immunodeficiency virus (HIV) may cause acquired immunodeficiency syndrome (AIDS). In that case the immune system of an organism, such as a human being, is weakened such that said system is not able to antagonize further life-threatening opportunistic infections. At present an HIV infection is said to be not curable, such that it is a main target to prevent or at least significantly slow down the proliferation of the corresponding virus. Since the treatment of an HIV infection is quite complex, combination therapies have been proposed. Combination therapies are therapies in which two or more pharmaceutical active agents are used. For example, in clinical trials a combination called "572-Trii" comprising 50 mg dolutegravir, 300 mg lamivudine and 600 mg abacavir seems to be very promising.

The pharmaceutical compositions, or dosage forms, according to the present invention and preferably comprising form HxA can additionally contain one or more further API(s), in addition to the dolutegravir forms disclosed herein, preferably in addition to form HxA. This further API can be any API that is usually combined with an API belonging to the group of integrase inhibitors, e.g. another API combined with dolutegravir. Such further API(s) are preferably selected from the group consisting of reverse transcriptase inhibitors (nucleoside/nucleotide reverse transcriptase inhibitors (NRTIs), and/or non-nucleoside/nucleotide reverse transcriptase inhibitors (NNRTIs)), protease inhibitors, fusion inhibitors (FIs), CCR5 antagonists, and integrase inhibitors (INIs) other than dolutegravir.

Examples of reverse transcriptase inhibitors are zidovudine; didanosine; stavudine; lamivudine; abacavir; adefovir; lobucavir; entecavir; apricitabine; emtricitabine; zalcitabine; dexelvucitabine; alovudine; amdoxovir; elvucitabine; tenofovir; festinavir; racivir; lersivirine; rilpivirine; etravirine; SP1093V and stampidine, or a pharmaceutically acceptable salt thereof.

Examples of protease inhibitors are saquinavir; ritonavir; nelfinavir; amprenavir; lopinavir; indinavir; nelfinavir; atazanavir; lasinavir; palinavir; fosamprenavir; darunavir; and tiprinavir.

If an incompatibility between the APIs is observed, then suitable measures that are known to a person skilled in the art for overcoming this incompatibility can be taken. Such suitable measures include physically separating the API(s) within the formulation or keeping low moisture (e.g. by avoiding water during formulation, and/or by storing the product in a moisture protective package).

In a preferred embodiment, the pharmaceutical compositions, or dosage forms, according to the present invention and preferably comprising form HxA can additionally contain one or more further API(s) selected from the group consisting of lamivudine, abacavir, tenofovir, efavirenz, GSK2248761, lersivirine, lopinavir, fosamprenavir, and atazanavir (or a pharmaceutically acceptable salt thereof).

In a further preferred embodiment, the pharmaceutical compositions, or dosage forms, according to the present invention and preferably comprising form HxA can additionally contain one or more further API(s) selected from the group consisting of rilpivirine, abacavir, lamivudine, tenofovir, ritonavir, emtricitabine, etravirine, lopinavir, darunavir (or a pharmaceutically acceptable salt thereof).

In a further embodiment, the pharmaceutical compositions, or dosage forms, according to the present invention and preferably comprising form HxA can additionally contain further API(s) selected from:
  at least one reverse transcriptase inhibitor comprising: zidovudine; didanosine; stavudine; lamivudine; abacavir; adefovir; lobucavir; entecavir; apricitabine; emtricitabine; zalcitabine; dexelvucitabine; alovudine; amdoxovir; elvucitabine; tenofovir; festinavir; racivir; lersivirine; rilpivirine; etravirine; SP1093V and/or stampidine, and/or
  at least one protease inhibitor comprising: saquinavir; ritonavir; nelfinavir; amprenavir; lopinavir, indinavir; nelfinavir; atazanavir; lasinavir; palinavir; fosamprenavir; darunavir and/or tiprinavir.

In a further preferred embodiment, the pharmaceutical compositions, or dosage forms, according to the present invention and preferably comprising form HxA can additionally contain lamivudine and abacavir (or a pharmaceutically acceptable salt thereof).

In a further preferred embodiment, the pharmaceutical compositions, or dosage forms, according to the present invention and preferably comprising form HxA can additionally contain tenofovir disoproxil and emtricitabine (or a pharmaceutically acceptable salt thereof).

In a further preferred embodiment, the pharmaceutical compositions, or dosage forms, according to the present invention and preferably comprising form HxA can additionally contain tenofovir alafenamide and emtricitabine (or a pharmaceutically acceptable salt thereof).

In a further preferred embodiment, the pharmaceutical compositions, or dosage forms, according to the present invention and preferably comprising form HxA can additionally contain rilpivirine hydrochloride.

Particularly preferred combinations are:
  Combination known as Trii-572: Dolutegravir/lamivudine/abacavir (50 mg/300 mg/600 mg)
  Combination: Dolutegravir/emtricitabine/tenofovir disoproxil fumarate (50 mg/200 mg/300 mg)
  Combination: Dolutegravir/emtricitabine/tenofovir disoproxil fumarate (50 mg/100 mg/150 mg)

Further combinations with dolutegravir are disclosed in e.g. WO 2011/094150, WO 2014/064409, WO 2014/184553 and WO 2015/022351.

The following non-limiting examples are illustrative for the disclosure.

EXAMPLES

PXRDs were obtained with an X'Pert PRO diffractometer (PANalytical, Almelo, The Netherlands) equipped with a theta/theta coupled goniometer in transmission geometry, programmable XYZ stage with well plate holder, Cu—K$\alpha_{1,2}$ radiation source (wavelength 0.15419 nm) with a focussing mirror, a 0.5° divergence slit, a 0.02° soller slit collimator and a 0.5° anti-scattering slit on the incident beam side, a 2 mm anti-scattering slit, a 0.02° soller slit collimator, a Ni-filter and a solid state PIXcel detector on the diffracted beam side. The diffractogram was recorded at room temperature at a tube voltage of 40 kV, tube current of 40 mA, applying a stepsize of 0.013° 2-Theta with 40 sec per step in the angular range of 2° to 40° 2-Theta. A typical precision of the 2-Theta values is in the range of ±0.2° 2-Theta. Thus, the diffraction peak of Form HxA that appears for example at 9.4° 2-Theta can appear between 9.2 and 9.6° 2-Theta on most X-ray diffractometers under standard conditions.

DSC was performed on a Mettler Polymer DSC R instrument. The samples were heated in 40 μL aluminum pans with pierced aluminum lids from 25 to 380° C. at a rate of 10° C./min. Nitrogen (purge rate 50 mL/min) was used as purge gas.

TGA was performed on a Mettler TGA/DSC 1 instrument. The samples were heated in 100 μL aluminum pans closed with aluminum lids. The lids were automatically pierced at the beginning of the measurements. The samples were heated from 25 to 250° C. at a rate of 10° C./min. Nitrogen (purge rate 50 mL/min) was used as purge gas.

Coulometric Karl-Fischer titrations were performed on a Metrohm 831 KF Coulometer.

The water values at varying relative humidities were obtained by recording moisture sorption/desorption isotherms with a SPS-11 moisture sorption analyzer (MD Messtechnik, Ulm, D). The samples were weighed into Teflon sample holders. The measurement cycles of the monohydrate of WO 2010/068253 A1 and the non-stoichiometric hydrate HxA of the present invention were started at 43% RH, decreased to 40% RH, further decreased in 10% steps to 10% RH, decreased in 5% steps to 0% RH, increased in 5% steps to 10% RH, further increased in 10% steps to 90% RH and subsequently increased to 95% RH, decreased again to 90% RH, decreased in 10% steps to 10% RH, further decreased in 5% steps to 0% RH, again increased in 5% steps to 10%, subsequently increased in 10% steps to 40% RH and finally increased to 43% RH. The measurement cycle of the monohydrate Hy1B of the present invention was started at 40% RH decreased in 10% steps to 0% RH, increased in 10% steps to 90% RH, decreased in 10% steps to 0% RH, and finally increased in 10% steps to 40% RH. The equilibrium condition for each step was set to a mass constancy of ±0.005% over 60 min. The temperature was 25±0.1° C. The water content of the samples was determined after the moisture sorption/desorption experiments with a TGA 7 system (Perkin Elmer, Norwalk, Conn., USA) using the Pyris 2.0 software. The samples were weighed into Al pans (50 μL). Dry nitrogen was used as purge gas (purge rate: 20 mL/min). The samples were heated from 25 to 200° C. using a heating rate of 10° C./min.

$^1$H-NMR spectra were recorded at 500 MHz on a Bruker Avance 500 instrument. Deuterated dimethyl sulfoxide (99.9% D) with tetramethylsilane as internal standard was used as solvent.

Example 1: Preparation of Dolutegravir Sodium Form HxA

A suspension of dolutegravir (6.006 g, 14.3 mmol, for example prepared in accordance with the procedures disclosed in examples 1a to 1k of WO 2010/068253 A1) in 78 mL methanol was cooled to 5±1° C. A refrigerated solution of sodium methoxide in methanol (25 weight %, 3.282 mL, 14.4 mmol) was dropwise added under stirring and the obtained suspension was further stirred at 5±1° C. for 2 h. Thereafter, the temperature of the suspension was increased to 25±1° C. in 1 h and stirred at the same temperature for additional 21 h. Finally, the crystals were collected by filtration and dried at RT under vacuum (20-30 mbar) for 21.5 h to obtain 5.843 g of dolutegravir sodium form HxA.

Yield: 92% of theory;

The PXRD of the obtained sample is displayed in FIG. 1 and the corresponding peak list is provided in table 2 below:

TABLE 2

PXRD peak list of dolutegravir sodium Form HxA obtained according to example 1

| Position [±0.2 °2Th.] | Relative Intensity [%] |
|---|---|
| 7.9 | 42 |
| 9.4 | 100 |
| 11.4 | 15 |
| 11.6 | 16 |
| 12.5 | 12 |
| 12.8 | 6 |
| 13.6 | 13 |
| 15.2 | 9 |
| 15.9 | 37 |
| 18.4 | 6 |
| 19.1 | 8 |
| 19.8 | 7 |
| 20.0 | 8 |
| 20.8 | 17 |
| 22.9 | 17 |
| 23.3 | 8 |
| 24.4 | 19 |
| 25.2 | 7 |
| 26.0 | 12 |
| 27.1 | 10 |
| 28.4 | 5 |
| 29.4 | 5 |

Example 2: Preparation of Dolutegravir Sodium Form HxA

A suspension of dolutegravir (1.007 g, 2.4 mmol, for example prepared in accordance with the procedures disclosed in examples 1a to 1k of WO 2010/068253 A1) in 13 mL methanol was adjusted to a temperature of 25±1° C. Solid sodium methoxide (assay: 95%, 0.136 g, 2.4 mmol) was added and the obtained suspension was further stirred at 25±1° C. for 2 hours. Finally, the crystals were collected by filtration and dried at RT under vacuum (20-30 mbar) for 19 h to obtain 0.965 g of dolutegravir sodium form HxA.

Yield: 91% of theory; Karl-Fischer titration: 0.9%; TGA: −0.9% (25-120° C., 10° C./min)

Example 3: Preparation of Dolutegravir Sodium Form HxA at Different Reaction Temperatures A suspension of dolutegravir (1.0 g, 2.4 mmol, for example prepared in accordance with the procedures disclosed in examples 1a to 1k of WO 2010/068253 A1) in 13 mL methanol was adjusted to a temperature according to table 3. Solid sodium methoxide (assay: 95%, 0.136 g, 2.4 mmol) was added and the obtained suspension was further stirred at the applied temperature for 2 hours. Finally, the crystals were collected by filtration and dried at RT under vacuum (20-30 mbar) for 19 h. The resulting materials were investigated by PXRD and the results are summarized in table 3.

TABLE 3

Crystalline forms obtained from reactions performed at different temperatures

| Example | Temperature | Assignment according to PXRD |
|---|---|---|
| 3a | 10 | HxA |
| 3b | 15 | HxA |
| 3c | 20 | HxA |
| 3d | 25 | HxA |
| 3e | 30 | HxA |
| 3f | 40 | HxA + anhydrous form of WO 2010/068253 A1 |
| 3g | 50 | anhydrous form of WO 2010/068253 A1 + HxA |

Example 4: Preparation of Dolutegravir Sodium Form HxA Using Different Concentrations A suspension of dolutegravir (1.0 g, 2.4 mmol respectively 0.5 g, 1.2 mmol, for example prepared in accordance with the procedures disclosed in examples 1a to 1 k of WO 2010/068253 A1) in an amount of methanol according to table 4 was adjusted to a temperature of 25±1° C. Solid sodium methoxide (assay: 95%, 0.136 g, 2.4 mmol respectively 0.068 g, 1.2 mmol) was added and the obtained suspension was further stirred at 25±1° C. for 2 hours. Finally, the crystals were collected by filtration and dried at RT under vacuum (20-30 mbar) for 19 h. The resulting materials were investigated by PXRD and the results are summarized in table 4.

TABLE 4

Crystalline forms obtained from reactions performed with different concentrations

| Example | $m_{dolutegravir}$ | $V_{MeOH}$ | Conc. | Assignment according to PXRD |
|---|---|---|---|---|
| 4a | 0.5 g | 50 mL | 10 g/L | anhydrous form of WO 2010/068253 A1 + HxA |
| 4b | 0.5 g | 17 mL | 30 g/L | anhydrous form of WO 2010/068253 A1 + HxA |
| 4c | 0.5 g | 10 mL | 50 g/L | anhydrous form of WO 2010/068253 A1 + HxA |
| 4d | 1.0 g | 13 mL | 75 g/L | HxA |
| 4e | 1.0 g | 10 mL | 100 g/L | HxA |

Example 5: Preparation of Dolutegravir Sodium Form Hy1B

Dolutegravir sodium form $S_{EtOH/H2O}$ (prepared according to example 6 herein) was subjected for 5 days to an atmosphere having a temperature of about 40° C. and a relative humidity of about 75% to obtain form Hy1B quantitatively.

Karl-Fischer titration: 3.3%; TGA: −3.3% (25-140° C.; 10° C./min)

The PXRD of the obtained sample is displayed in FIG. 4 and the corresponding peak list is provided in table 5 below:

TABLE 5

PXRD peak list of dolutegravir sodium Form Hy1B obtained according to example 4

| Position [±0.2 °2Th.] | Relative Intensity [%] |
|---|---|
| 6.3 | 22 |
| 7.4 | 100 |
| 10.9 | 18 |
| 11.1 | 18 |
| 12.7 | 19 |
| 16.2 | 30 |
| 18.6 | 24 |
| 18.8 | 28 |
| 19.7 | 15 |
| 20.5 | 17 |
| 21.0 | 19 |
| 22.1 | 13 |
| 23.0 | 29 |
| 24.0 | 14 |
| 24.9 | 10 |
| 26.5 | 13 |

Example 6: Preparation of Dolutegravir Sodium Form $S_{EtOH/H2O}$

A suspension of dolutegravir (2.004 g, 4.8 mmol, for example prepared in accordance with the procedures disclosed in examples 1a to 1k of WO 2010/068253 A1) in 80 mL ethanol was adjusted to a temperature of 25±1° C. Solid sodium ethoxide (assay: 95%, 0.516 g, 7.2 mmol) was added and the obtained suspension was further stirred at 25±1° C. for 2 h. Finally, the crystals were collected by filtration and dried at RT under vacuum (20-30 mbar) for 42 h to obtain 2.105 g of dolutegravir sodium form $S_{EtOH/H2O}$.

Yield: 96% of theory; Karl-Fischer titration: 0.9%; TGA: −3.4% (25-120° C., 10° C./min)

The PXRD of the obtained sample is displayed in FIG. 7 and the corresponding peak list is provided in table 6.

TABLE 6

PXRD peak list of dolutegravir sodium Form $S_{EtOH/H2O}$ obtained according to example 5

| Position [±0.2 °2Th.] | Relative Intensity [%] |
|---|---|
| 6.5 | 16 |
| 7.0 | 100 |
| 10.6 | 7 |
| 11.0 | 14 |
| 13.3 | 16 |
| 16.0 | 20 |
| 18.0 | 12 |
| 19.1 | 15 |
| 20.3 | 24 |
| 20.8 | 8 |
| 22.6 | 19 |

Example 7: Preparation of Dolutegravir Sodium Form $S_{EtOH/H2O}$ at Different Reaction Temperatures A suspension of dolutegravir (0.5 g, 1.2 mmol for example prepared in accordance with the procedures disclosed in examples 1a to 1k of WO 2010/068253 A1) in 50 mL ethanol was adjusted to a temperature according to table 7. Solid sodium ethoxide (assay: 95%, 0.085 g, 1.2 mmol) was added and the obtained suspension was further stirred at the applied temperature for 2 hours. Finally, the crystals were collected by filtration and dried at RT under vacuum (20-30 mbar) for 20 h. The resulting materials were investigated by PXRD and the results are summarized in table 7.

TABLE 7

Crystalline forms obtained from reactions performed at different temperatures

| Example | Temperature | Assignment according to PXRD |
|---|---|---|
| a | 5 | HxA |
| b | 15 | HxA |
| c | 25 | HxA |
| d | 35 | HxA |
| e | 45 | HxA |
| f | 60 | anhydrous form of WO 2010/068253 A1 + HxA |

Reference Example 1—Preparation of Dolutegravir Sodium Monohydrate of WO 2010/068253 A1

A mixture of dolutegravir (1.998 g, 4.8 mmol, for example prepared in accordance with the procedures disclosed in examples 1a to 1k of WO 2010/068253 A1) in 40 mL THF/water (8:2=V:V) was adjusted to a temperature of 30° C. After the addition of 2.4 mL 2N NaOH the mixture was stirred at 25±1° C. for 2 h. The obtained crystals were collected by filtration, washed with 10 mL THF/water (8:2=V:V) and dried at 85° C. under vacuum (20-30 mbar) for 18 h to obtain 1.845 g of dolutegravir sodium in form of the monohydrate disclosed in WO 2010/068253 A1.

Example 8: Preparation of Dolutegravir Sodium

Form I (i.e. the Anhydrous Form of Dolutegravir Sodium Disclosed in WO 2010/068253 A1):

DLG free acid (31.21 g; 74.4 mmol, for example prepared in accordance with the procedures disclosed in examples 1a to 1 k of WO 2010/068253 A1) was heated in the mixture of ethanol/water 9:1 (1500 ml) at reflux temp. Sodium hydroxide (1M; 75 ml) solution was added; the suspension clears briefly before 'form I' begins to precipitate. Suspension was cooled to ambient temperature; then filtered (washed with ethanol) and dried in vaccum at ambient temperature to give the product.

Form HxA (for Example Prepared in Accordance with the Procedures Disclosed in Examples 1 and 2 Herein Above):

DLG free acid (50.33 g; 120 mmol, for example prepared in accordance with the procedures disclosed in examples 1a to 1k of WO 2010/068253 A1) was suspended in methanol (650 ml; 77 mg/ml); cooled to 0-5° C., followed by the slow (20') addition of cooled (5° C.) solution of NaOMe (in MeOH; 25 wt %). Suspension was stirred at 0-5° C. for 2 h, followed by stirring at ambient temperature overnight. Suspension was filtered and dried in vaccum at ambient temperature to give the product.

Form I and form HxA, prepared as described in Example 8, were used in the following Examples 9 to 16.

Example 9: Determination of Particle Morphology of Form I and Form HxA

Figure 13:
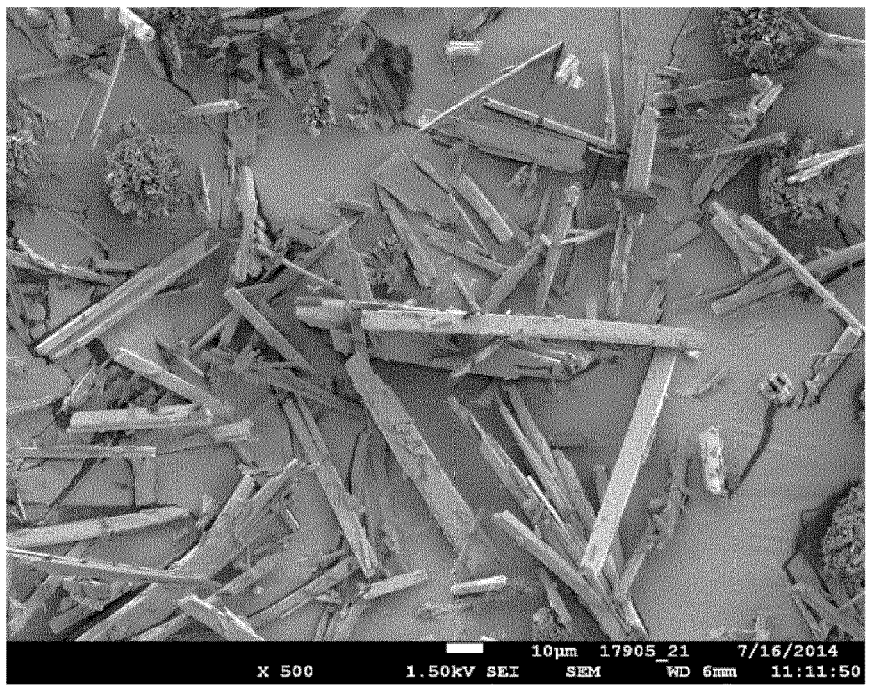
FIG. 13: Scanning electron micrograph images of crystalline dolutegravir Form I at 500× magnification (FIG. 13 a) and 1.500× magnification (FIG. 13 b)
Figure 13:
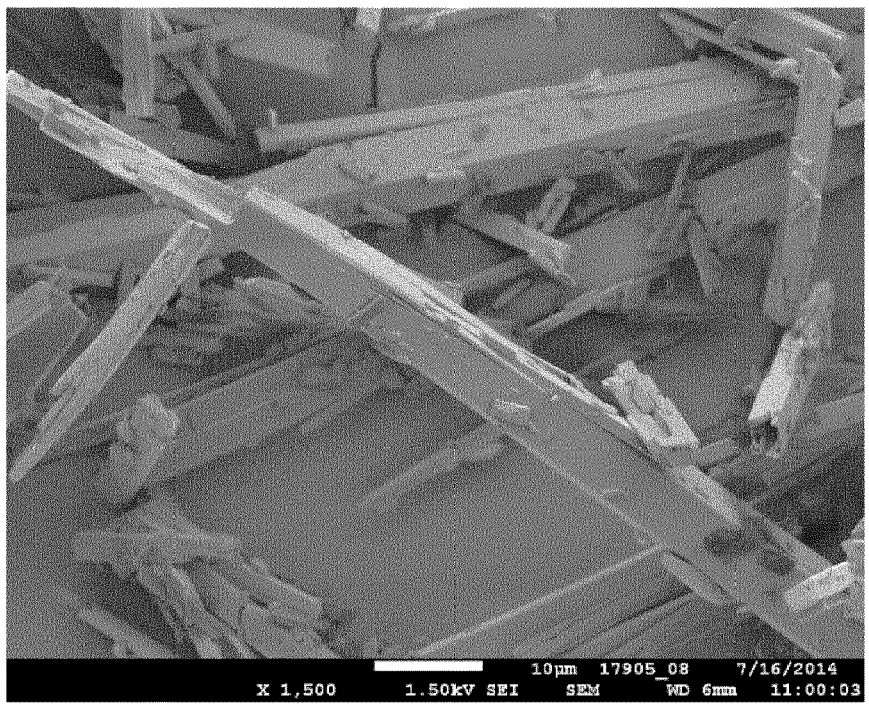

A figure of the morphology of Form I and form HxA is depicted in FIG. 13 (Form I) and 14 (form HxA), at different magnifications (500× magnification (Form I), 1.500× magnification (Form I and form HxA), and 5.000× magnification (form HxA)).

As can be seen from the respective figures, Form I of dolutegravir appeared as a long needle like crystals with needle lengths up to approximately 70 μm. Such needle like crystals are generally known to be unsuitable for direct compression due to poor flow properties, more emphasized cohesive and adhesive properties in powder mixtures, inadequate compressibility and compactibility related to weak particle contact and larger elastic relaxation in decompression phase (Rasenack N, Muller B W, Crystal habit and tableting behavior, Int. J. Pharm 244 (2002)).

In contrast, HxA form has thin-plate like morphology of primary particles. The crystal structure is layered with particle sizes of about 5 μm. This different external appearance of HxA form seems to be related to pseudo polymorphism. Plate-like crystals in comparison to needle-like crystals undergo greater densification and plastic deformation, which could be benefit in formation of coherent compacts during compression. Furthermore, crystals of HxA form are also more homogeneous concerning single particle shape with more uniform particle size distribution. The particles are only weakly agglomerated, and these agglomerates are of overall uniform appearance.

Example 10: Particle Size Determination

Particle size of dolutegravir Form I and form HxA, as determined with laser diffraction method, is summarized in Table 8. Particle size distribution was determined by laser diffraction methods of particles dispersed in a medium in which dolutegravir is not soluble (such as hexane, silicone or paraffine oil) with addition of a suitable surfactant (such as DSSS (Dioctyl Sodium Sulfosuccinate)) to ensure proper dispersion of primary particles. Dolutegravir dispersion was sonicated for 3 to 5 minutes.

Particle size of HxA dolutegravir is well below 10 μm, which is in accordance with SEM observation. This particle size was achieved with crystallization only, i.e. was achieved without applying size reduction steps like micronisation. As a state of art, size reduction steps, in particular micronization procedures, can be variable (large inter batch variability in PSD) and can result in formation of agglomerates with adhesive and electrostatic properties.

TABLE 8

API particle size as determined with laser diffraction.

| | API particle size as determined with laser diffraction | | |
|---|---|---|---|
| | d0.1 (μm) | d0.5 (μm) | d0.9 (μm) |
| Form HxA | 1.3 | 3.1 | 7.4 |
| Form I: | 3.5 | 10 | 40 |

Example 11: Compressibility Testing of Different Dolutegravir Sodium Forms

Direct compression is the simplest process of tablet preparation being more economical and less stressful to ingredients in terms of heat and moisture. However, good flow properties of the powder mixture are required for a successful tableting process. For direct compression, substances (APIs and excipients) with good flow characteristics are necessary. If flow of the powder mixture is not sufficient, other (more time consuming) manufacturing techniques such as wet or dry granulation need to be used for tablet preparation.

Powders with particles below 50 microns will generally exhibit irregular or no flow. On the other side, an increase in particle size will be proportional to an increase in powder flow (up to a certain dimension). In addition to particle size also the particle shape can greatly influence the powder flow. The more spherical particles are, the better the flow is. An elongated particles shape and small particle sizes could therefore cause difficulty during tableting and may cause high tablet weight and strength variations as well as unacceptable content uniformity (Shayne, Cox, Gad; 2008 Pharmaceutical Manufacturing Handbook: Production and Processes; John Wiley & Sons; 233-265; 879-931)). Hence, designing API with a suitable particle size and shape combined with a proper excipient choice can greatly simplify tableting preparation.

As described in Example 8 herein above, the sodium salt of dolutegravir was prepared in two polymorphic forms (Form I and form HxA). Unexpectedly, significantly different particle design was observed for both forms. As outlined above (cf. Example 9), Form HxA has a plate like morphology which could have better flow properties and higher densification in comparison to the needle like crystals of Form I. To evaluate the flowabilty/compressibility of both forms a common index such as the compressibility index was measured for both forms of dolutegravir API. Compressibilty index is an indirect measure of different powder properties such as size, shape, surface area, cohesiveness etc. (PhEur). Bulk (Vb) and tapped (Vt) volume were measured for several batches of both forms and the compressibilty index (%) is determined based on Vb and Vt. 250 mL volumetric cylinder with test samples weight approximately 25 g were used. The compressibility index was calculated according to formula ((Vb−Vt)/Vb). The results are presented in table 9.

It can be seen that the HxA form of dolutegravir sodium had better flowability properties and is (according to the PhEur flowability scale) considered as a "poor" to "passable" flowing powder (compressibility index ranging from 22-29) while Form I has very poor flowing properties (compressibility index ranging from 32-35; table 9). Surprisingly, although the particle size for HxA is in micron range (see Example 10), it has a better compressibility index and powder flow which implies a less adhesive nature of the plate-like crystals (Table 9 and 11). Furthermore, HxA form has lower bulk and tapped volumes, which are related to better particle packing and higher densification of the plate-like crystals. This unexpected property is beneficial for compaction since it provides more intensive inter-particles contacts and formation of dense tablets.

TABLE 9

Bulk volume, tapped volume and compressibility index for several dolutegravir Na API batches Form HxA and From I.

| Form | Bulk volume (ml/g) | Tapped volume (ml/g) | Compressibility index(%) | Flow character according to PhEur* |
|---|---|---|---|---|
| Form I | 4.89 | 3.23 | 34 | Very poor |
|  | 5.55 | 3.79 | 32 | Very poor |
|  | 7.00 | 4.56 | 35 | Very poor |
| Form HxA | 4.02 | 2.86 | 29 | Poor |
|  | 2.88 | 2.14 | 26 | Poor |
|  | 3.30 | 2.60 | 21 | Passable |
|  | 2.89 | 2.25 | 22 | Passable |

*PhEur Chapter 2.9.36 Powder flow

Example 12: Powder Mixture Characterization of Dolutegravir Na Form HxA and Form I with Chosen Excipients In addition to the API powder characteristics (cf. Example 11 above), also the properties of an API/excipient mixture was tested. API (Form I or HxA) was mixed with excipients used in immediate release solid dosage forms (dilutent/filler, binder, disintegrant, . . . etc.) (Table 10).

TABLE 10

Composition of powder mixture and tablets prepared with dolutegravir Na Form I or HxA

|  | Mg/tbl |
|---|---|
| Dolutegravir sodium: either | 52.60 |
| Form HxA (cf. Examples 1, 2, 8) or |  |
| Form I (cf. Example 8) |  |
| D-mannitol (Pearlitol SD 200) | 145.40 |
| Microcrystalline cellulose (Avicel PH 102) | 60.00 |
| Povidone (Plasdone K29/32) | 15.00 |
| Sodium starch glycolate (Primojel) | 21.00 |
| Sodium stearyl fumarate | 6.00 |
| Final tablet mass | 300.00 |

In addition to the compressibility index, also powder flow through an orifice and angle of response of powder mixture were measured (Table 11). Powder flow through an orifice and angle of response are additional indices commonly used to evaluate powder mixture prior tableting processes. Results from these testing usually give a prediction whether or not a powder mixture can be used for direct compression. Powder flow through an orifice and angle of response were measured according to Ph. Eur (using Pharmatest PTG-2 with 10 mm pouring nozzle and 100 ml plastic funnel).

TABLE 11

Bulk volume, tapped volume, compressibility index, powder flow and angle of response data for dolutegravir Na Form HxA/excipient and Form I/excipient dry powder mixture

|  | Form I (API/excipient dry powder mixture) | Form HxA (API/excipient dry powder mixture) |
|---|---|---|
| Bulk volume (ml/g) | 2.43 | 2.22 |
| Tapped volume (ml/g) | 1.66 | 1.76 |
| Compressibility index(%) | 32 | 21 |
| Powder flow (g/s) | 0.1 | 0.8 |
| Angle of repose (°) | 39 | 36 |

Although an improvement of flowabilty was seen for the powder mixture of dolutegravir API (form I and form HxA) with other excipients (some fillers are designed to improve powder characteristics for easier tableting), the flowabilty of the mixture with form I was still considered as "poor" while for form HxA it was "passable".

Example 13: Preparation of Solid Dosage Form Formulations with Dolutegravir Sodium Form HxA (Example 8)

Dolutegravir sodium HxA, mannitol and cellulose were mixed together and sieved through 0.7 mm mesh sieve. Povidone and sodium starch glycolate were added and further mixed. Then, sieved sodium stearyl fumarate was added and the mixture was additionally blended.

The final blend was directly compressed into tablets using round 10 mm punches.

Example 14: Preparation of Solid Dosage Form Formulation with Dolutegravir Sodium Form I (Example 8)

Direct compression of the reference example powder mixture with form I was not possible due to poor filling of powder into the tableting die. A sufficient tablet mass could not be obtained even at slow tableting speeds. Due to poor compressibility and flow characteristics of the powder mixture with dolutegravir sodium form I, wet granulation was necessary to obtain good flowing material for successful tableting. Dolutegravir Na, mannitol and cellulose were mixed together and sieved through 0.7 mm mesh sieve. Povidone and sodium starch glycolate were added and further mixed. Powder mixture was granulated with water and dried until LOD (loss on drying) of granulate was below 1%. Granulate was sieved and sieved sodium stearyl fumarate was added and the mixture was additionally blended. The final blend was compressed into tablets using round 10 mm punches.

Example 15: Results of Dissolution Test, Content Uniformity Assay, and Stress Stability Test Comparative dissolution test was performed in 0.9% NaCl, pH 6.8 phosphate buffer and water media, analyzed with Apparatus 2 at 50 rpm. Results are presented in the following table.

TABLE 12

Dissolution in 0.9% NaCl, pH 6.8 phosphate buffer and water media analyzed with Apparatus 2 at 50 rpm for sample "Form HxA" in comparison to marketed reference product (TIVICAY) is shown.

| Time (min) | 0.9% NaCl | | pH 6.8 | | water | |
|---|---|---|---|---|---|---|
| | Form HxA | Tivicay | Form HxA | Tivicay | Form HxA | Tivicay |
| 10 | 52.4 | 56.9 | 56.3 | 35.8 | 103.5 | 97.2 |
| 20 | 68.5 | 64.3 | 69.7 | 54.9 | 106.5 | 101.6 |
| 30 | 76.0 | 65.5 | 74.4 | 60.0 | 106.2 | 102.4 |
| 45 | 84.2 | 66.2 | 79.0 | 63.7 | 106.0 | 102.3 |
| 60 | 89.1 | 67.5 | 82.9 | 65.2 | 107.1 | 102.4 |
| infinity | 91.7 | 68.6 | 85.4 | 66.8 | 107.0 | 102.2 |

As shown in Table 12, the solid pharmaceutical dosage form comprising dolutegravir sodium form HxA surprisingly reaches a faster dissolution compared to the marketed reference product TIVICAY (which comprises dolutegravir sodium in form I).

TABLE 13

Content uniformity results (assay of Dolutegravir) by LC method

| | Content uniformity | |
|---|---|---|
| | Mean (%) | % RSD |
| Form I | 88.2 | 2.8 |
| Form HxA | 99.2 | 1.7 |

Also surprisingly, the content uniformity of solid dosage forms comprising the crystalline form HxA is improved compared to reference form "Form I" (table 13) although the solid oral dosage form comprising Form I was prepared by wet granulation (which is applied amongst others in order to facilitate and ensure a proper homogeneity).

TABLE 14

Stress stability results (60° C., 75% RH, 14 days open dish): dolutegravir impurities by LC method

| | impurities, sum % | |
|---|---|---|
| | initial | 60/75 14 d |
| Form I | 0.41 | 0.32 |
| Form HxA | 0.14 | 0.11 |

Also with regard to stress stability, a dosage form comprising form HxA exhibited excellent chemical stability (cf. example 15, table 14).

LC Method for Assay and Impurities:

One 50 mg tablet is dissolved in 100 ml of solvent and analyzed by liquid chromatography under the following experimental conditions:

Mobile phase: Ammonnium acetate buffer pH=4.8 (0.77 g/l) and acetonitrile, gradient elution. Column dimensions 100×2.1 mm with 1.7 micrometer particles of type C18. Column is maintained at 40° C., flow: 0.3 milliliter per minute and injection volume 1 microliter. Detection is with an ultraviolet detector, quantitation is per external standard.

Example 16: Compatibility of Dolutegravir Form HxA with Other APIs

Further experiments were conducted to assess compatibility of Dolutegravir form HxA with other APIs. To this purpose, binary mixtures of dolutegravir sodium HxA with APIs were produced and exposed to stress test (60° C. and two moisture levels: 29% RH and 75% RH) for 7 days. The results show that dolutegravir sodium is compatible with a number of APIs (table 15) and may be formulated as one-tablet-therapy with different HIV substances. Interestingly, dolutegravir Na (form HxA) was found to be incompatible with tenofovir diisoproxil fumarate and this incompatibility was exaggerated by moisture. To formulate dolutegravir sodium (form HxA) and tenofovir diisoproxil fumarate into a single dosage form, one should take into account this incompatibility. It could be overcome, for instance, by physically separating both APIs within the formulation or by a keeping low moisture (for instance avoiding water during formulation steps and by storing the product in a moisture protective package).

TABLE 15

Compatibility results: % impurities by LC method

| Binary mixtures: | Impurities (%) | | |
|---|---|---|---|
| dolutegravir HxA + API | initial | 60/29 | 60/75 |
| Abacavir sulfate | | no decomposition | no decomposition |
| Lamivudine | | no decomposition | no decomposition |
| Rilpivirine HCl | | no decomposition | no decomposition |
| Tenofovir disoproxil fumarate | 0.65% | sum = 3.5% | sum = 24.6% |
| Emtricitabine | | no decomposition | no decomposition |
| Etravirine | | no decomposition | no decomposition |
| Ritonavir | | no decomposition | no decomposition |

The invention claimed is:

1. A crystalline form of dolutegravir sodium of formula (I)

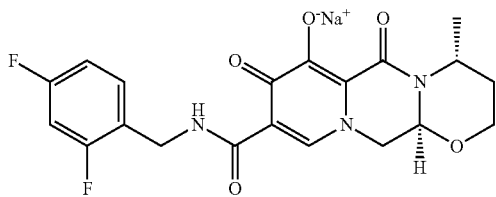

characterized by a powder X-ray diffractogram comprising peaks at 2-Theta angles of 7.9±0.2°, 9.4±0.2°, 12.5±0.2°, 15.9±0.2° and 20.8±0.2°, when measured with Cu-Katz radiation having a wavelength of 0.15419 nm at room temperature wherein the crystalline form comprises 0.2 to 0.7 mol of water per mol dolutegravir sodium of formula (I) when measured at a relative humidity from 30 to 70% and a temperature of 25±0.1° C.

2. A process for the preparation of the crystalline form according to claim 1 comprising:
   (i) providing a suspension or a solution of dolutegravir of formula (II)

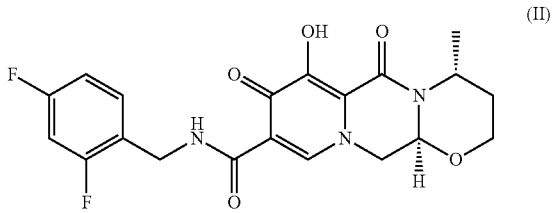 [SMILES: C[C@@H]1CCO[C@H]2Cn3cc(C(=O)NCc4ccc(F)cc4F)c(=O)c(O)c3C(=O)N12]

in a solvent, wherein the suspension or the solution comprises more than 50 g dolutegravir of formula (II) per liter solvent,
   (ii) reacting dolutegravir of formula (II) with sodium methoxide at a temperature of not more than 30° C. and
   (iii) precipitating dolutegravir sodium.

3. The process according to claim 2, further comprising
   (iv) separating at least a portion of the crystalline form of dolutegravir sodium from its mother liquor.

4. A pharmaceutical composition comprising an effective amount of the crystalline form according to claim 1 or mixtures thereof and at least one pharmaceutically acceptable excipient.

5. The pharmaceutical composition according to claim 4, wherein the one or more pharmaceutically acceptable excipients are selected from the group consisting of diluent, filler, binder, disintegrant, lubricant, and surfactant, wherein:
   the diluent/filler is selected from the group consisting of sugar, cellulose or a derivative thereof, starch, calcium phosphate, calcium or magnesium carbonate, and mixtures thereof;
   the binder is selected from the group consisting of povidone, tragacanth, sodium alginate, gum arabic, starch pregelatinized, gelatin and cellulosic derivates;
   the disintegrant is selected from the group consisting of croscarmellose sodium, sodium carboxymethyl starch, cross-linked polyvinylpyrrolidone, sodium carboxymethyl glycolate, sodium starch glycolate, low-substituted hydroxypropyl cellulose, citric acid and sodium bicarbonate;
   the lubricant is selected from the group consisting of colloidal silicon dioxide, talc, stearic acid, magnesium stearate, calcium stearate, zinc stearate, glyceryl behenate, sodium stearyl fumarate, polyethylene glycol, and silicon dioxide;
   the surfactant is selected from the group consisting of tween, polyoxyethylene-polyoxypropylene copolymer and sodium lauryl sulfate.

6. The pharmaceutical composition according to claim 4, wherein said composition comprises mannitol, microcrystalline cellulose, povidone, sodium starch glycolate, and sodium stearyl fumarate, as the pharmaceutically acceptable excipients.

7. A process for preparing oral dosage forms, comprising the steps of:
   (i) providing the crystalline form of dolutegravir sodium of formula (I) of claim 1, and one or more pharmaceutically acceptable excipients selected from the group consisting of diluent, filler, binder, disintegrant, lubricant, and surfactant;
   (ii) formulating the crystalline form of dolutegravir sodium of formula (I) and pharmaceutically acceptable excipients of step (i) into an oral dosage form, wherein step (ii) does not comprise a wet granulation step;
   (iii) obtaining said oral dosage form, and optionally further comprising
   (iv) applying a coating onto the oral dosage form obtained in step (iii).

8. The process according to claim 7, wherein the process does not include a dolutegravir particle size reduction step.

9. The pharmaceutical composition according to claim 4 for use in a method for treating immunodeficiency virus type 1 (HIV-1) infection in human.

* * * * *